US012667280B2

(12) United States Patent
Huang et al.

(10) Patent No.:　US 12,667,280 B2
(45) Date of Patent:　Jun. 30, 2026

(54) ESTIMATION DEVICE, ESTIMATION METHOD, AND PROGRAM RECORDING MEDIUM

(71) Applicant: NEC Corporation, Tokyo (JP)

(72) Inventors: Chenhui Huang, Tokyo (JP);
Kenichiro Fukushi, Tokyo (JP);
Zhenwei Wang, Tokyo (JP); **Hiroshi
Kajitani, Tokyo (JP); Fumiyuki Nihey**,
Tokyo (JP); Kentaro Nakahara, Tokyo
(JP)

(73) Assignee: NEC CORPORATION, Tokyo (JP)

( * ) Notice: Subject to any disclaimer, the term of this
patent is extended or adjusted under 35
U.S.C. 154(b) by 450 days.

(21) Appl. No.: 18/027,781

(22) PCT Filed: Oct. 2, 2020

(86) PCT No.: PCT/JP2020/037607
§ 371 (c)(1),
(2) Date: Mar. 22, 2023

(87) PCT Pub. No.: WO2022/070416
PCT Pub. Date: Apr. 7, 2022

(65) Prior Publication Data
US 2023/0329585 A1　　Oct. 19, 2023

(51) Int. Cl.
*A61B 5/11*　　(2006.01)
*A61B 5/107*　　(2006.01)

(52) U.S. Cl.
CPC ............ *A61B 5/112* (2013.01); *A61B 5/1074*
(2013.01)

(58) Field of Classification Search
CPC ..... A61B 5/112; A61B 5/1074; A61B 5/1036;
A61B 5/1038; A61B 5/4595
See application file for complete search history.

(56) References Cited

U.S. PATENT DOCUMENTS

| | | | |
|---|---|---|---|
| 6,639,140 B2 | 10/2003 | Mishima | |
| 6,867,361 B2 | 3/2005 | Nishitani et al. | |
| 10,105,571 B2 * | 10/2018 | Solinsky | ............ A63B 69/0028 |
| 10,820,836 B2 | 11/2020 | Winter | |

(Continued)

FOREIGN PATENT DOCUMENTS

| | | |
|---|---|---|
| JP | 2018-011890 A | 1/2018 |
| JP | 2018-094305 A | 6/2018 |

(Continued)

OTHER PUBLICATIONS

KR20200081117translation (Year: 2020).*

(Continued)

*Primary Examiner* — Devin B Henson
(74) *Attorney, Agent, or Firm* — Sughrue Mion, PLLC

(57)　　　　ABSTRACT

An estimation device that includes a detection unit that
detects a terminal stance period from time-series data of
sensor data based on a physical quantity related to move-
ment of a foot measured by a sensor provided at a foot
portion, a feature amount extraction unit that extracts a
feature amount from an angular waveform in a coronal plane
during the terminal stance period, and a presumption unit
that estimates a degree of pronation/supination of the foot by
using the feature amount extracted from the angular wave-
form in the coronal plane.

17 Claims, 23 Drawing Sheets

SUPINATION

NORMAL

(56)                    References Cited

U.S. PATENT DOCUMENTS

| | | | |
|---|---|---|---|
| 2005/0126370 A1 | 6/2005 | Takai et al. | |
| 2008/0258921 A1* | 10/2008 | Woo ......................... | G10H 1/40 |
| | | | 482/8 |
| 2012/0253234 A1* | 10/2012 | Yang .................... | A61B 5/1038 |
| | | | 600/595 |
| 2016/0100801 A1 | 4/2016 | Clark et al. | |

FOREIGN PATENT DOCUMENTS

| | | | | |
|---|---|---|---|---|
| KR | 20200081117 A | * | 7/2020 | ............. A61B 5/112 |
| WO | 2018/164157 A1 | | 9/2018 | |

OTHER PUBLICATIONS

International Search Report for PCT Application No. PCT/JP2020/037607, mailed on Nov. 17, 2020.
English translation of Written opinion for PCT Application No. PCT/JP2020/037607, mailed on Nov. 17, 2020.

Bruce A. Macwilliams et al., "A simple expression of supination and pronation", Conference: Gait and Clinical Movement Analysis Society, Jan. 31, 2012, the Internet <URL: https://www.researchgate.net/profile/Bruce_MacWilliams/publication/281274184_Poster_A_simple_expression_of_supination_and_pronation/links/55ddf7e608aeaa26af0f1f90/Poster-A-simple-expression-of-supination-and-pronation.pdf>.
Hylton B. Menz et al., "Association of Planus Foot Posture and Pronated Foot Function With Foot Pain: The Framingham Foot Study", Arthritis Care & Research, Dec. 31, 2013, vol. 65, No. 12, pp. 1991-1999.
Larry P. Brown et al., "Locomotor Biomechanics and Pathomechanics: A Review", The Journal of Orthopaedic and Sports Physical Therapy, Jul. 1, 1987, vol. 9, No. 1, pp. 3-10.
US Office Action for U.S. Appl. No. 18/411,241, mailed on Feb. 5, 2026.
US Office Action for U.S. Appl. No. 18/411,324, mailed on Feb. 6, 2026.

* cited by examiner

Fig.4

SUPINATION

PRONATION

SUPINATION

NORMAL

PRONATION

Fig.10

CPEI
PITCH ANGLE
FEATURE AMOUNT

15

LEARNING
DEVICE

| USERS | MAKERS | FOOTWEAR | DATE AND TIME OF MEASUREMENT | OPEI ESTIMATION VALUE | |
|---|---|---|---|---|---|
| A | X COMPANY | X1 | 2019 9 25 | +8.2 | ... |
| | Y COMPANY | Y1 | 2019 9 26 | +7.8 | ... |
| | Z COMPANY | Z1 | 2019 9 27 | +8.5 | ... |
| | X COMPANY | X1 | 2019 9 28 | +8.3 | ... |
| | Y COMPANY | Y1 | 2019 9 29 | +7.9 | ... |
| | Z COMPANY | Z1 | 2019 9 30 | +8.4 | ... |
| | ... | ... | ... | ... | ... |
| | X COMPANY | X1 | 2020 9 28 | +9.5 | ... |
| | Y COMPANY | Y1 | 2020 9 29 | +7.9 | ... |
| | Z COMPANY | Z1 | 2020 9 30 | +8.2 | ... |
| ... | ... | ... | ... | ... | ... |
| B | X COMPANY | X1 | 2019 9 25 | +10.3 | ... |
| | Y COMPANY | Y1 | 2019 9 26 | +9.8 | ... |
| | Z COMPANY | Z1 | 2019 9 27 | +10.1 | ... |
| ... | ... | ... | ... | ... | ... |

ESTIMATION DEVICE, ESTIMATION METHOD, AND PROGRAM RECORDING MEDIUM

This application is a National Stage Entry of PCT/JP2020/037607 filed on Oct. 2, 2020, the contents of all of which are incorporated herein by reference, in their entirety.

TECHNICAL FIELD

The present disclosure relates to an estimation device or the like that estimates a state of a foot.

BACKGROUND ART

With increasing interest in healthcare that performs physical condition management, a service that measures a gait including a walking characteristics and provides information corresponding to the gait to a user has attracted attention. For example, a device has been developed in which a load measurement device or an inertial measurement device is mounted on footwear such as shoes for analyzing the gait of the user. If the state of the foot can be estimated based on the gait, an appropriate measure can be taken when an abnormality in the foot is observed. For example, if the degree of pronation or supination of the foot can be estimated, actions for reducing the progression of symptoms can be taken.

PTL 1 discloses a foot abnormality analysis device including a member with which a sole of a foot is in contact, a sensor that measures a force acting on a predetermined position of the member, and a control device that determines whether there is an abnormality based on an output from the sensor. The device of PTL 1 determines a centroid point, a centroid line, an arch, and a bone axis of the foot, and compares the determined centroid point, centroid line, arch, and bone axis of the foot with normal data to determine the presence or absence of abnormality.

CITATION LIST

Patent Literature

PTL 1: JP 2018-094305 A

SUMMARY OF INVENTION

Technical Problem

In the method of PTL 1, in order to measure the degree of pronation/supination of the foot, data measured by a plurality of pressure sensors that determine a centroid point, a centroid line, an arch, and a bone axis of the foot is used. Therefore, the method of PTL 1 has a problem that many sensors are required to determine whether there is an abnormality of the foot, and the configuration is complicated.

An object of the present disclosure is to provide an estimation device and the like capable of estimating a degree of pronation/supination of a foot with a simple configuration.

Solution to Problem

An estimation device according to an aspect of the present disclosure includes a detection unit that detects a terminal stance period from time-series data of sensor data based on a physical quantity related to movement of a foot measured by a sensor provided at a foot portion, a feature amount extraction unit that extracts a feature amount from an angular waveform in a coronal plane during the terminal stance period, and a presumption unit that estimates a degree of pronation/supination of the foot by using the feature amount extracted from the angular waveform in the coronal plane.

In an estimation method according to an aspect of the present disclosure, a computer executes processes including detecting a terminal stance period from time-series data of sensor data based on a physical quantity related to a movement of a foot measured by a sensor provided at a foot portion, extracting a feature amount from an angular waveform in a coronal plane during the terminal stance period, and estimating a degree of pronation/supination of the foot using the feature amount extracted from the angular waveform in the coronal plane.

A program according to an aspect of the present disclosure causes a computer to execute processes including detecting a terminal stance period from time-series data of sensor data based on a physical quantity related to a movement of a foot measured by a sensor provided at a foot portion, extracting a feature amount from an angular waveform in a coronal plane during the terminal stance period, and estimating a degree of pronation/supination of the foot using the feature amount extracted from the angular waveform in the coronal plane.

Advantageous Effects of Invention

According to the present disclosure, it is possible to provide an estimation device and the like capable of estimating the degree of pronation/supination of the foot with a simple configuration.

BRIEF DESCRIPTION OF DRAWINGS

FIG. 4 is a conceptual diagram for explaining a gait event detected by the estimation device of the estimation system according to the first example embodiment.

FIG. 10 is a conceptual diagram illustrating an example of learning of a presumption model used by the estimation device of the estimation system according to the first example embodiment.

FIG. 11 is a conceptual diagram illustrating an example of estimation of the degree of pronation/supination of the foot by the estimation device of the estimation system according to the first example embodiment.

FIG. 21 is a conceptual diagram illustrating an example of a table in which data based on the estimation result regarding the degree of pronation/supination of the foot estimated by the estimation device of the estimation system according to the first example embodiment is compiled into a database.

EXAMPLE EMBODIMENT

Figure 1:
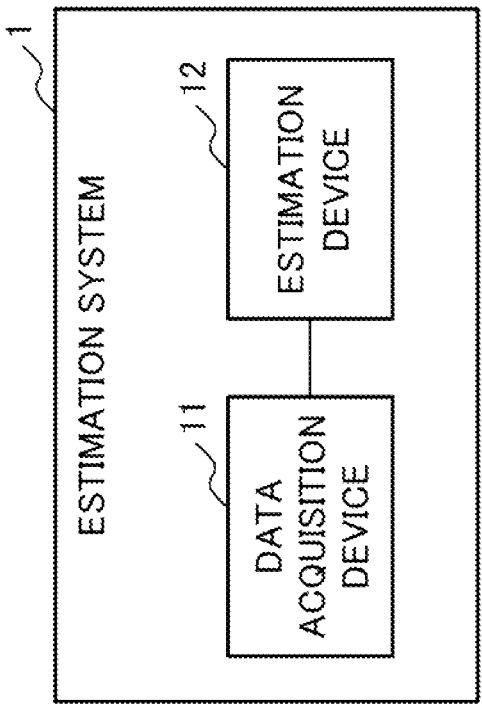
FIG. 1 is a block diagram illustrating an example of a configuration of an estimation system according to a first example embodiment.

Hereinafter, example embodiments of the present invention will be described with reference to the drawings. Note that the example embodiments described below have technically preferable limitations for carrying out the present invention, but the scope of the invention is not limited to the following description. In all the drawings used in the following description of the example embodiments, the same reference numerals are assigned to the same parts unless there is a particular reason. Further, in the following example embodiments, repeated description of similar configurations and operations may be omitted.

First Example Embodiment

An estimation system according to a first example embodiment of the present disclosure will be described with reference to the drawings. The estimation system of the present example embodiment measures a feature of a gait pattern (also referred to as a gait) of a user and analyzes the measured gait to estimate a state of a foot. Specifically, the estimation system of the present example embodiment estimates a degree of pronation/supination of the foot based on sensor data related to a movement of the foot. According to the present example embodiment, a system in which the right foot is a reference foot and the left foot is an opposite foot will be described. The method according to the present example embodiment can also be applied to a system in which the left foot a reference foot and the right foot is an opposite foot.

(Configuration)

FIG. 1 is a block diagram illustrating a configuration of an estimation system 1 according to the present example embodiment. The estimation system 1 includes a data acquisition device 11 and an estimation device 12. The data acquisition device 11 and the estimation device 12 may be connected by wire or wirelessly. Furthermore, the data acquisition device 11 and the estimation device 12 may be configured by a single device. Alternatively, the data acquisition device 11 may be excluded from the configuration of the estimation system 1, and only the estimation device 12 may constitute the estimation system 1.

The data acquisition device 11 is installed on a foot portion. For example, the data acquisition device 11 is installed in footwear such as shoes. According to the present example embodiment, an example in which the data acquisition device 11 is disposed at a position on the back side of the arch of foot will be described. The data acquisition device 11 includes an acceleration sensor and an angular velocity sensor. The data acquisition device 11 measures a physical quantity such as an acceleration (also referred to as a spatial acceleration) measured by an acceleration sensor and an angular velocity (also referred to as a spatial angular velocity) measured by an angular velocity sensor, as a physical quantity related to the movement of the foot of the user wearing the footwear. The physical quantity related to the movement of the foot measured by the data acquisition device 11 includes not only the acceleration and the angular velocity but also the velocity and the angle calculated by integrating the acceleration and the angular velocity. The data acquisition device 11 converts the measured physical quantity into digital data (also referred to as sensor data). The data acquisition device 11 transmits the converted sensor data to the estimation device 12. For example, the data acquisition device 11 is connected to the estimation device 12 via a mobile terminal (not illustrated) carried by the user.

The mobile terminal (not illustrated) is a communication device that can be carried by a user. For example, the mobile terminal is a portable communication device having a communication function, such as a smartphone, a smart watch, or a mobile phone. The mobile terminal receives, from the data acquisition device 11, the sensor data related to the movement of the user's foot. The mobile terminal transmits the received sensor data to a server or the like on which the estimation device 12 is installed. Note that the function of the estimation device 12 may be implemented by application software or the like installed in the mobile terminal. In this case, the mobile terminal processes the received sensor data by the application software or the like installed therein.

The data acquisition device 11 is implemented by, for example, an inertial measurement device including an acceleration sensor and an angular velocity sensor. An example of the inertial measurement unit is an inertial measurement device (IMU). The IMU includes a three-axis acceleration sensor and a three-axis angular velocity sensor. Furthermore, examples of the inertial measurement device include a vertical gyro (VG), an attitude heading (AHRS), and a global positioning system/inertial navigation system (GPS/INS).

Figure 2:
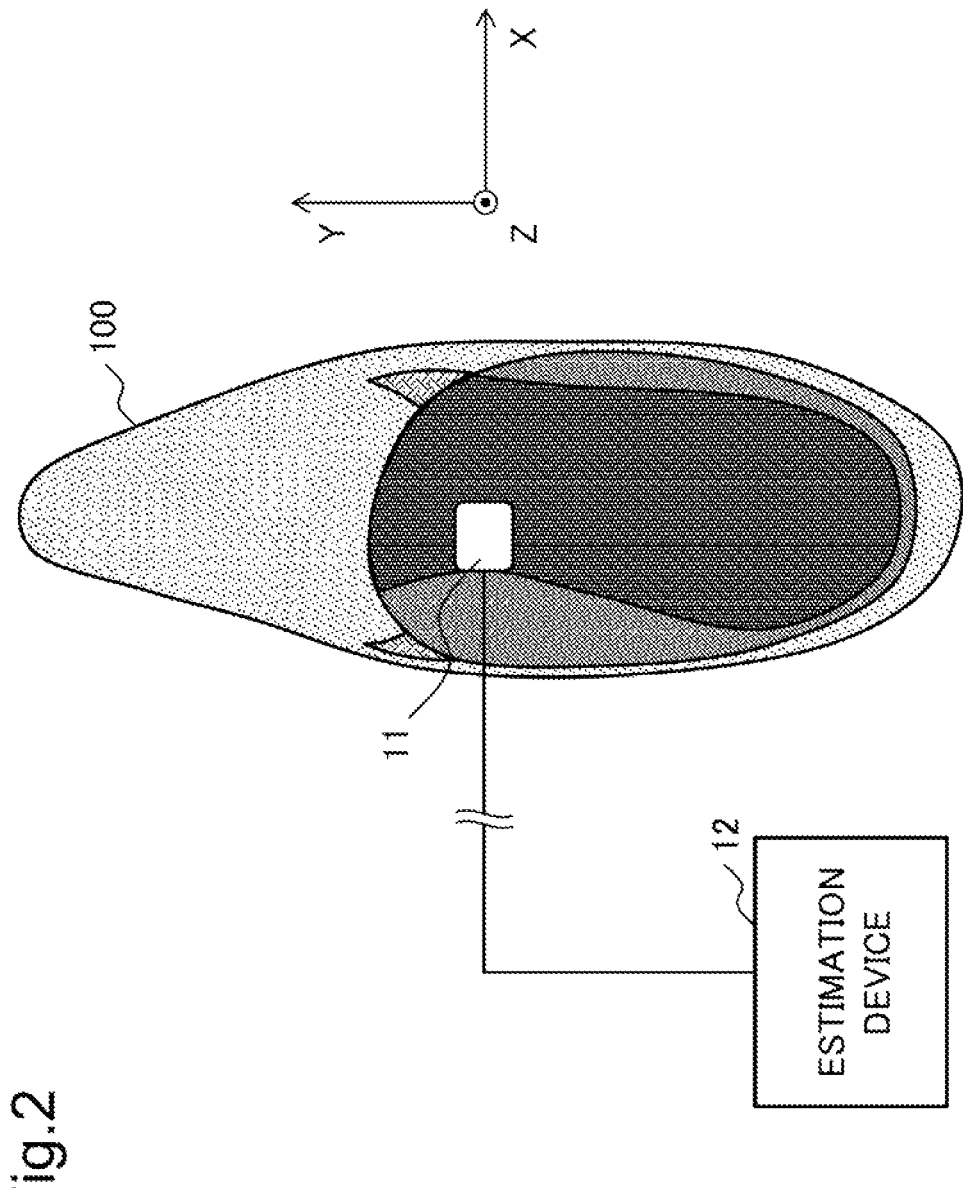
FIG. 2 is a conceptual diagram illustrating an example in which a data acquisition device of the estimation system according to the first example embodiment is disposed in footwear.

FIG. 2 is a conceptual diagram illustrating an example in which the data acquisition device 11 is disposed in a shoe 100. In the example of FIG. 2, the data acquisition device 11 is installed in an arrangement corresponding to the back side of the arch of foot. For example, the data acquisition device 11 is disposed in an insole to be inserted into the shoe 100. For example, the data acquisition device 11 is disposed on the bottom surface of the shoe 100. For example, the data acquisition device 11 is embedded in the main body of the shoe 100. The data acquisition device 11 may be detachable from the shoe 100 or may not be detachable from the shoe 100. Note that the data acquisition device 11 may be installed at a position other than the back side of the arch of the foot as long as the sensor data regarding the movement of the foot can be acquired. Furthermore, the data acquisition device 11 may be installed on a sock worn by the user or on a decorative article such as an anklet worn by the user. In addition, the data acquisition device 11 may be directly attached to a foot or may be embedded in a foot. FIG. 2 illustrates an example in which the data acquisition device 11 is installed in the shoe 100 on the right foot side, but the data acquisition device 11 may be installed in the shoe 100 for both feet. If the data acquisition device 11 is installed in the shoe 100 for both feet, the state of the foot can be estimated based on the movement of the both feet.

Figure 3:
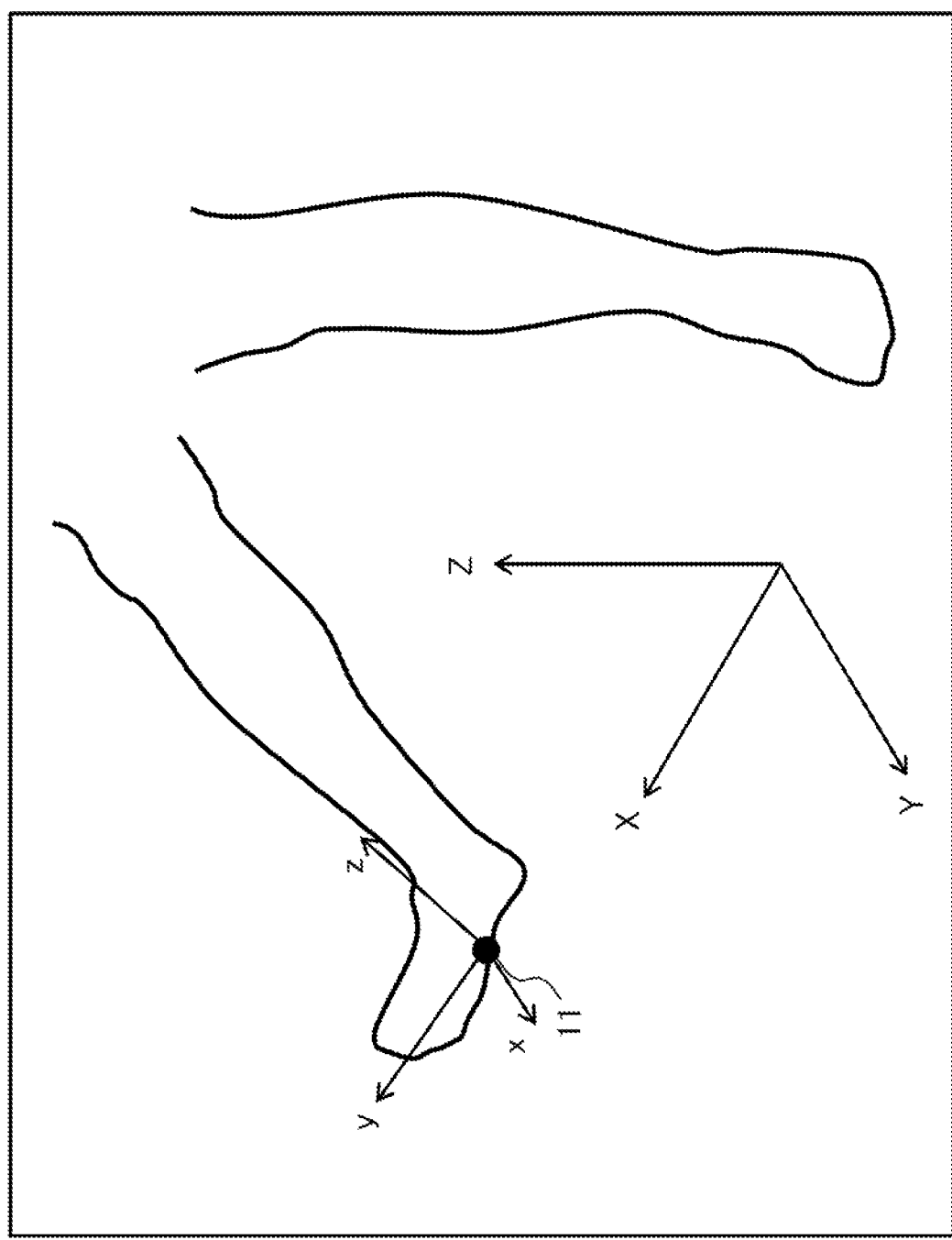
FIG. 3 is a conceptual diagram for describing a relationship between a local coordinate system and a world coordinate system set in the data acquisition device of the estimation system according to the first example embodiment.

FIG. 3 is a conceptual diagram for describing a local coordinate system (x-axis, y-axis, and z-axis) set in the data acquisition device 11 and a world coordinate system (X axis, Y axis, and Z axis) set with respect to the ground, in a case where the data acquisition device 11 is installed on the back side of the arch of foot. In the world coordinate system (X axis, Y axis, and Z axis), in a state where the user is standing upright, a lateral direction of the user is set to the X-axis direction (rightward direction is positive), a front direction of the user (traveling direction) is set to the Y-axis direction (forward direction is positive), and a gravity direction is set to the Z-axis direction (vertically upward direction is positive). According to the present example embodiment, the local coordinate system including an x direction, a y direction, and a z direction based on the data acquisition device 11 is set. According to the present example embodiment, rotation around the x-axis is defined as roll, rotation around the y-axis is defined as pitch, and rotation around the z-axis is defined as yaw.

Figure 4:
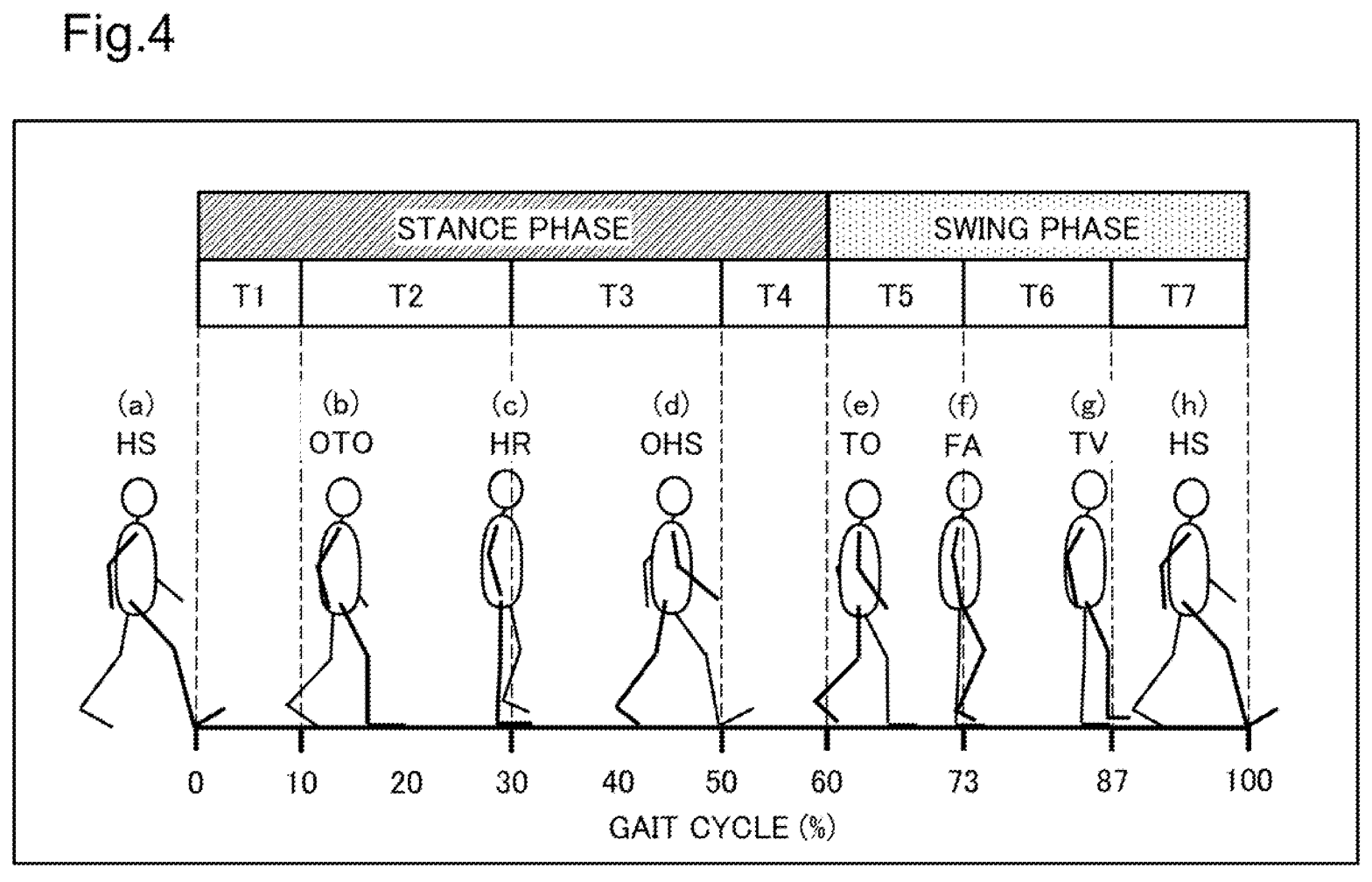

FIG. 4 is a conceptual diagram for explaining one gait cycle with the right foot as a reference. The horizontal axis of FIG. 4 is a gait cycle normalized with one gait cycle of the right foot as 100%, with a starting point at a time point when the heel of the right foot lands on the ground and an ending point at a time point when the heel of the right foot next lands on the ground. The one gait cycle of one foot is roughly divided into a stance phase in which at least a part of the back side of the foot is in contact with the ground and a swing phase in which the back side of the foot is not in contact with the ground. The stance phase is further subdivided into an initial stance period T1, a mid-stance period T2, a terminal stance period T3, and a pre-swing period T4. The swing phase is further subdivided into an initial swing period T5, a mid-swing period T6, and a terminal swing period T7. Note that the start of a gait waveform for one gait cycle does not have to be the heel strike as long as the period of the terminal stance period can be specified.

FIG. 4(*a*) illustrates an event (heel strike) in which the heel of the right foot touches the ground (HS: Heel Strike). FIG. 4(*b*) illustrates an event (opposite toe off) in which the toe of the left foot moves away from the ground while the ground contact surface of the sole of the right foot is in contact with the ground (OTO: Opposite Toe Off). FIG. 4(*c*) illustrates an event (heel lift) in which the heel of the right foot is lifted while the ground contact surface of the sole of the right foot is in contact with the ground (HR: Heel Rise). FIG. 4(*d*) is an event (opposite heel strike) in which the heel of the left foot is grounded (OHS: Opposite Heel Strike). FIG. 4(*e*) illustrates an event (toe off) in which the toe of the right foot is separated from the ground in a state where the ground contact surface of the sole of the left foot is in contact with the ground (TO: Toe Off). FIG. 4(*f*) illustrates an event (foot adjacent) in which the left foot and the right foot are adjacent with each other in a state where the ground contact surface of the sole of the left foot is grounded (FA: Foot Adjacent). FIG. 4(*g*) illustrates the event (tibia vertical) that the right tibia is approximately perpendicular to the ground in a state where the sole of the left foot is grounded (TV: Tibia Vertical). FIG. 4(*h*) illustrates the event (heel strike) that the heel of the right foot touches the ground (HS: Heel Strike). FIG. 4(*h*) is relevant to the end point of the gait cycle starting from FIG. 4(*a*) and is relevant to the start point of the next gait cycle. According to the present example embodiment, as will be described later, the degree of pronation/supination of the foot is estimated using the feature amount extracted from the time-series data of the pitch angle of 30 to 50% of the gait cycle (the terminal stance period T3).

Figure 5A:
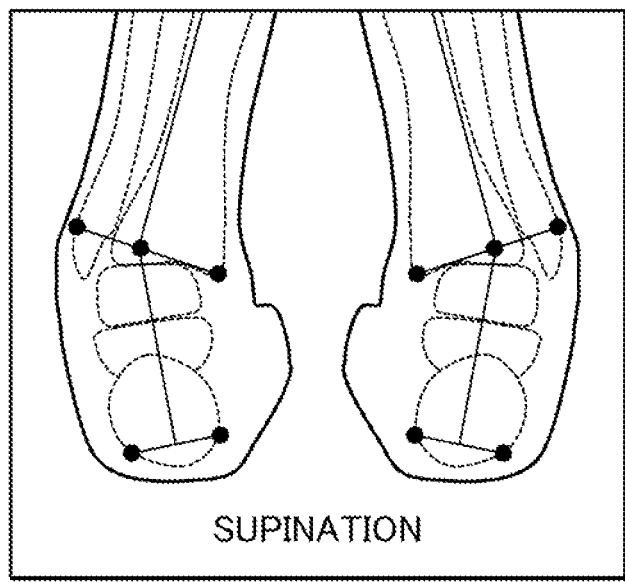
FIG. 5A is a conceptual diagram for explaining supination of the foot.
Figure 5B:
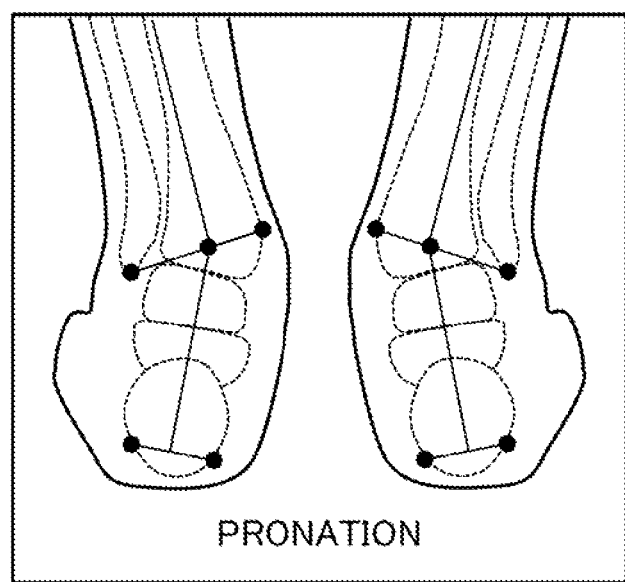
FIG. 5B is a conceptual diagram for explaining pronation of the foot.

The pronation/supination of the foot will be described with reference to the drawings. FIG. 5A is a conceptual diagram for explaining supination of the foot. FIG. 5B is a conceptual diagram for explaining pronation of the foot. The pronation/supination of the foot is a triplanar motion that simultaneously includes motion in the coronal plane, sagittal and horizontal planes. According to the present example embodiment, the pronation/supination of the foot is regarded as coronal plane movement of the subtalar joint. According to the present example embodiment, since the angle in the coronal plane when the person is standing upright is used, the sensor data in the local coordinate system is converted into the world coordinate system when calculating the pitch angle. The supination is a motion including adduction, plantarflexion, and inversion of the foot portion. The pronation is a motion including abduction, dorsiflexion, and eversion. For example, a foot having a large degree of pronation and fixed in this state is referred to as a pronation foot. Similarly, a foot having a large degree of supination and fixed in this state is referred to as a supination foot.

Figure 6:
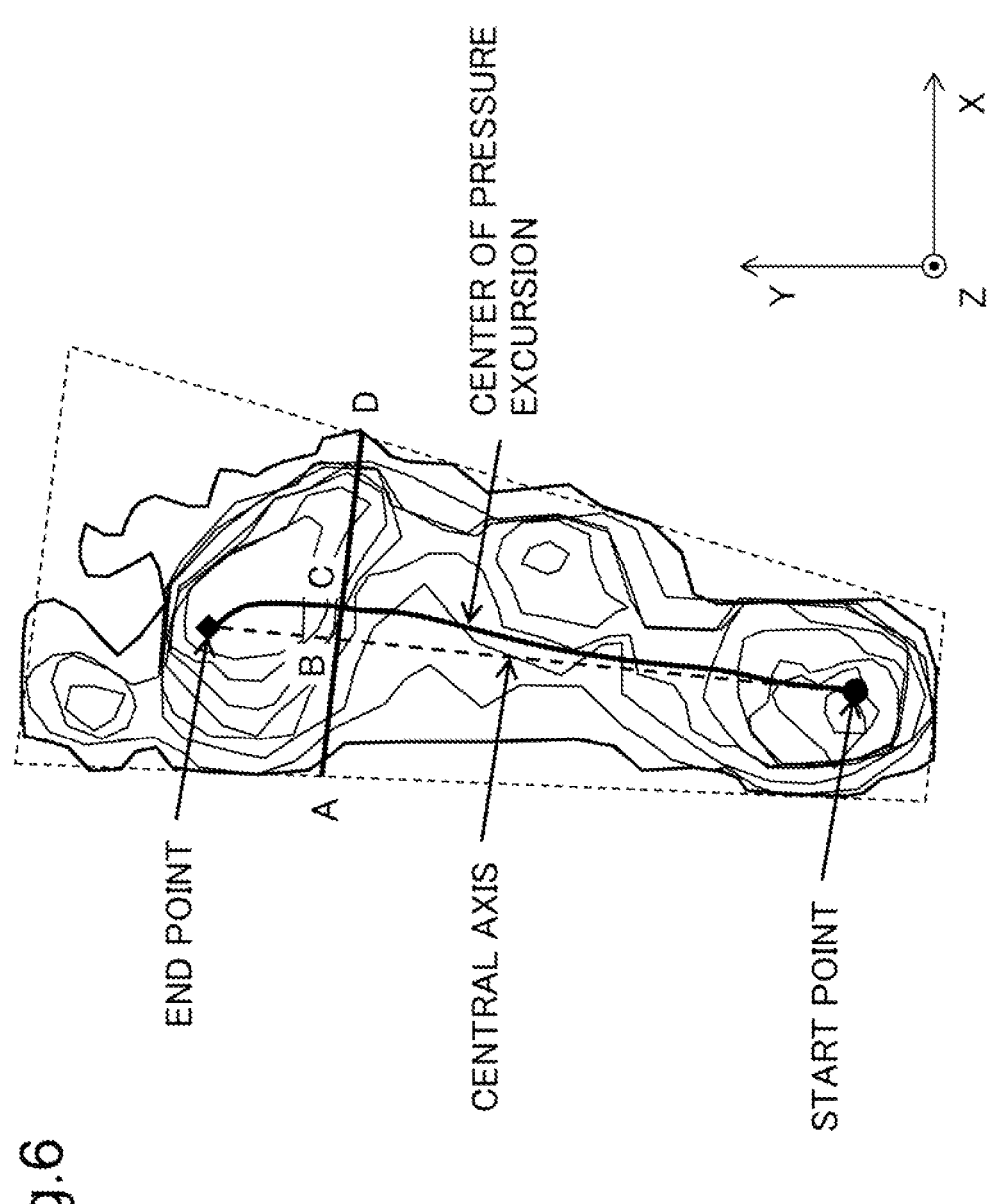
FIG. 6 is a conceptual diagram for explaining a center of pressure excursion index (CPEI) derived from a foot pressure distribution.

The degree of pronation/supination of the foot can be evaluated by the Center of Pressure Excursion Index (CPEI). FIG. 6 is a conceptual diagram for explaining the CPEI. FIG. 6 illustrates a center of pressure (CoP) trajectory of a foot superimposed on the foot pressure distribution. The center of pressure excursion is a trajectory obtained by connecting the maximum point (maximum load center) of the foot pressure along the Y-axis direction from the heel strike point (start point) to the toe separation point (end point) on a line obtained by cutting the foot pressure distribution in the floor surface (XY plane) along the coronal plane (ZX plane). The straight line connecting the start point and the end point is referred to as a central axis (also referred to as a construction line). A trapezoid whose base is perpendicular to the central axis surrounds the contour of the foot, and ⅓ of the portion in the forward direction of the foot is cut along a cutting line parallel to the base of the trapezoid. Of intersections of the trapezoid and the cutting line, the point inside the foot is defined as A, and the point outside the foot is defined as D. The intersection of the central axis and the cutting line is defined as B, and the intersection of the center of pressure excursion and the cutting line is defined as C. The line segment BC is referred to as a center of pressure excursion (CPE). The line segment AD is relevant to a foot width. The ratio between the CPE (the length of the line segment BC) and the foot width (the length of the line segment AD) is relevant to the trajectory of the center of pressure excursion index CPEI (Equation 1).

$$CPEI = CPE/Foot\ width \times 100 \qquad (1)$$

However, the start point and the end point, the manner of surrounding the trapezoid, the manner of cutting the trapezoid, and the like are merely examples, and are not limited to the above definitions.

Figure 7A:
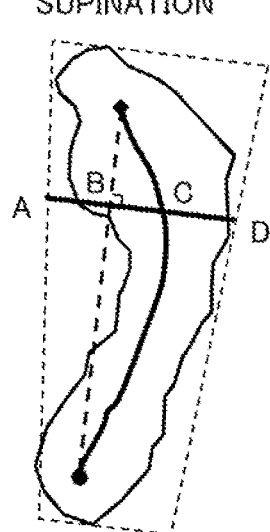
FIG. 7A is a conceptual diagram for explaining CPEI according to the progress of supination of the foot.
Figure 7B:
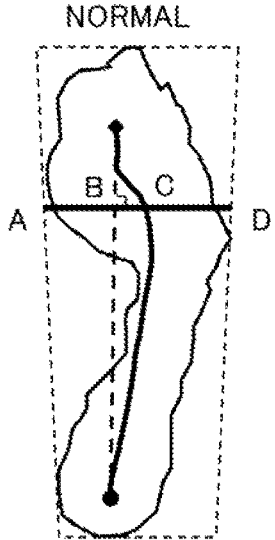
FIG. 7B is a conceptual diagram for explaining CPEI of the foot in normal state.
Figure 7C:
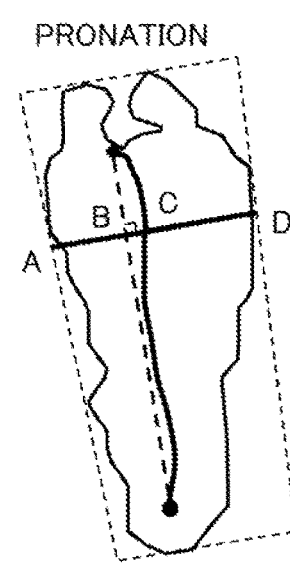
FIG. 7C is a conceptual diagram for explaining CPEI according to the progress of pronation of the foot.

FIG. 7A is a conceptual diagram for explaining CPEI according to the progress of supination of the foot. FIG. 7B is a conceptual diagram for explaining CPEI of the foot in normal state. FIG. 7C is a conceptual diagram for explaining CPEI according to the progress of pronation of the foot. In the case of supination, the CPE (length of the line segment BC) tends to be longer and the foot width (length of the line segment AD) tends to be smaller than those in the normal state. On the other hand, in the case of pronation, the CPE (length of the line segment BC) tends to be shorter and the foot width (length of the line segment AD) tends to be larger than those in the normal state. In other words, it can be determined that a state in which the CPEI is excessively large is supination and a state in which the CPEI is excessively small is pronation. According to the present example embodiment, when the CPEI is equal to or more than 20, it is classified into supination, when the CPEI is 9 to 20, it is classified into normal classification, and when the CPEI is equal to or less than 9, it is classified into pronation. The determination criterion based on the value of CPEI is an example of the degree of pronation/supination of the foot, and the determination criterion of the degree of pronation/supination of the foot is not limited as described above.

The estimation device 12 acquires sensor data regarding the movement of the foot of the user. The estimation device 12 estimates the degree of the pronation/supination of the foot using a gait waveform of a rotation angle (also referred to as a pitch angle) of the foot in a coronal plane (zx plane)

among waveforms (also referred to as gait waveforms) based on time-series data of the acquired sensor data. In other words, the estimation device 12 estimates the degree of pronation/supination of the foot using the time-series data of the pitch angle which is the rotation angle of the foot around the Y axis. Specifically, the estimation device 12 estimates the degree of pronation/supination of the foot using the feature amount extracted from the terminal stance period T3 in the time-series data of the pitch angle.

For example, the estimation device 12 is implemented in a server (not illustrated) or the like. For example, the estimation device 12 may be enabled by an application server. For example, the estimation device 12 may be enabled by application software or the like installed in a mobile terminal (not illustrated).

Figure 8:
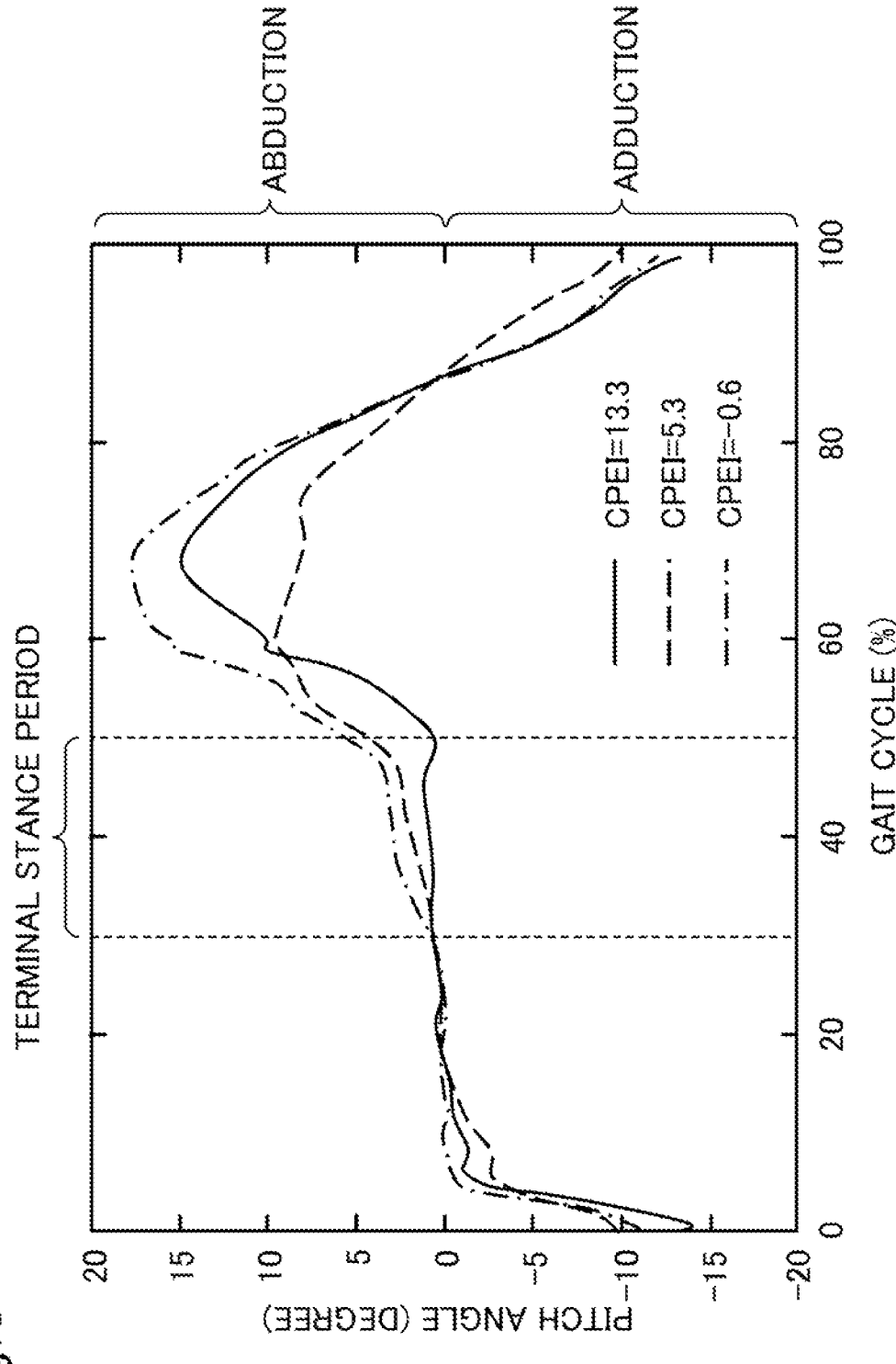
FIG. 8 is an example of a graph of time-series data of a pitch angle for one gait cycle of the right foot, from which a feature amount used by the estimation device of the estimation system according to the first example embodiment to estimate the degree of pronation/supination of the foot is extracted.

FIG. 8 is a graph of an example of time-series data of the pitch angle for one gait cycle of the right foot measured for three subjects. FIG. 8 illustrates waveforms of pitch angles of a subject with a CPEI of 13.3 (solid line), a subject with a CPEI of 5.3 (broken line), and a subject with a CPEI of −0.6 (alternate long and short dash line). The greater the CPEI, the greater the tendency of supination, and the smaller the CPEI, the greater the tendency of pronation. The pitch angle is set such that rotation in the abduction direction (counterclockwise rotation about the Y axis) is positive, and rotation in the adduction direction (clockwise rotation about the Y axis) is negative.

As illustrated in FIG. 8, the difference in characteristics between pronation and supination appears in the period of the terminal stance period. In the terminal stance period, the pitch angle tends to tilt to the minus side in the case of supination, and tends to tilt to the plus side in the case of pronation. That is, the degree of pronation/supination of the foot can be estimated by using the feature amount of the pitch angle at the terminal stance period. For example, the estimation device 12 uses an integral value of the pitch angle at the terminal stance period as the feature amount to estimate a stance degree of pronation/supination of the foot. For example, the estimation device 12 estimates the degree of pronation/supination of the foot using an average value such as an arithmetic average or a weighted average of the pitch angle at the terminal stance period as the feature amount. Note that the above feature amount is an example, and does not limit the feature amount used by the estimation device 12 to estimate the degree of pronation/supination of the foot.

Figure 9:
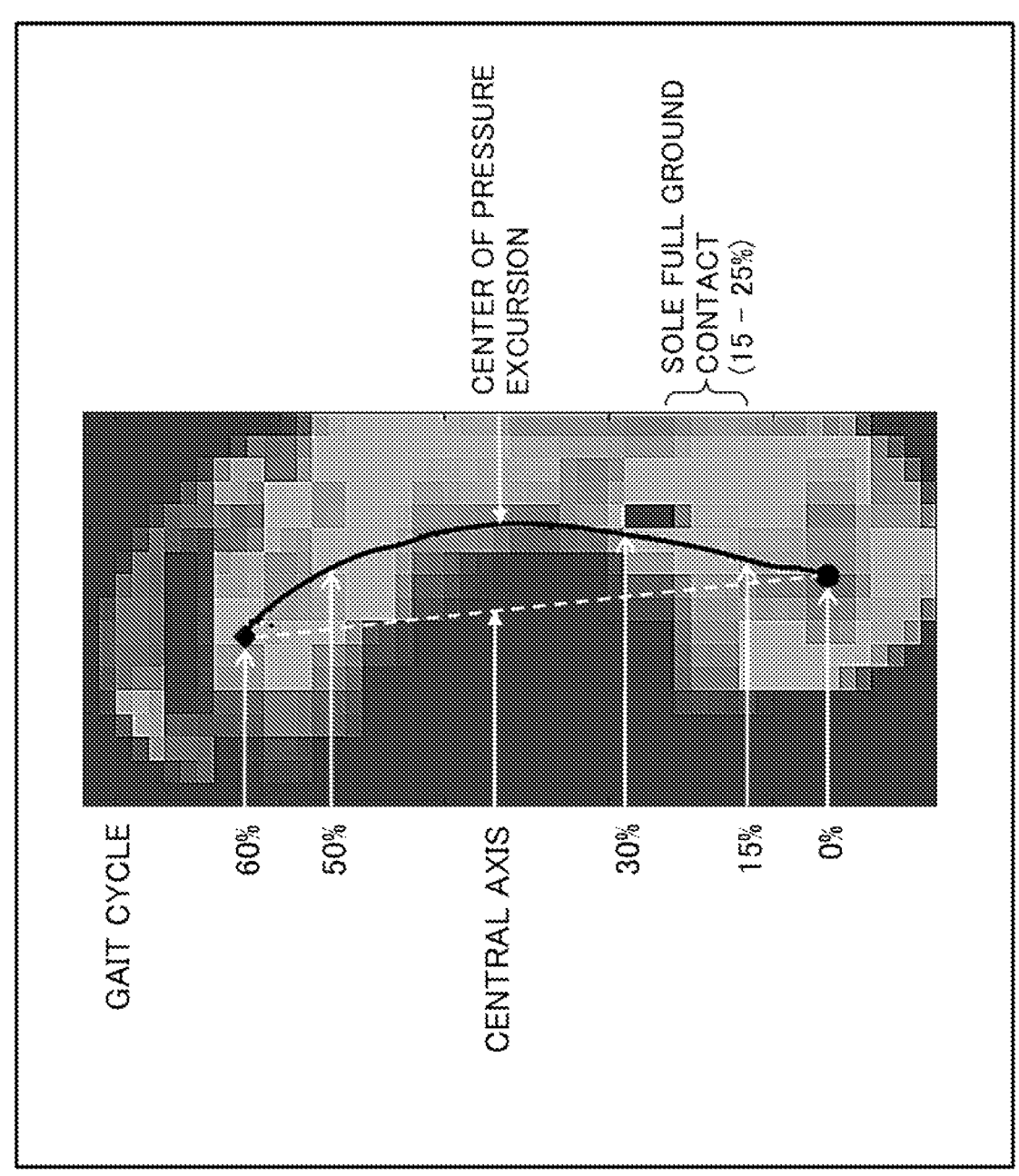
FIG. 9 is a conceptual diagram for describing a correspondence relationship between the center of pressure excursion and the gait cycle.

FIG. 9 is a conceptual diagram for describing a correspondence relationship between the center of pressure excursion and the gait cycle. FIG. 9 illustrates a foot pressure distribution measured for a certain subject, and a central axis and a center of pressure excursion in the foot pressure distribution. On the left side of the foot pressure distribution, the gait cycle corresponding to the center of pressure excursion is illustrated.

15 to 25% of the gait cycle is a state of a sole full ground contact (Foot flat) of the right foot. The sole full ground contact means that the entire ground contact surface of the sole is grounded. In a state of the sole full ground contact (foot flat), the pitch angle is 0 degrees. 30% of the gait cycle is relevant to the timing of heel lift. From 30 to 50% of the gait cycle, the area of the sole contacting the ground gradually decreases as the weight moves from the heel side to the toe side of the right foot. 60% of the gait cycle is the timing of the toe off the ground at which the toe of the right foot leaves the ground.

If the foot has a tendency of supination, the curve of the CPEI becomes steep because the contact portion between the sole and the ground is biased to the outside of the foot. In this case, there is a tendency of adduction, and the pitch angle decreases at the terminal stance period which is 30 to 50% of the gait cycle. When the degree of supination is excessive, the pitch angle may be negative. On the other hand, when there is a tendency of pronation, the contact portion between the sole and the ground is biased to the inner side of the foot, so that the curve of the CPEI becomes loose. In this case, there is a tendency of abduction, and the pitch angle increases at the terminal stance period which is 30 to 50% of the gait cycle.

According to the present example embodiment, a presumption model is generated in advance by learning a data set of a feature amount extracted from the time-series data of the pitch angle measured by the data acquisition device 11 and CPEI obtained from the foot pressure distribution measured by a pressure sensor. For example, the presumption model for outputting the degree of pronation/supination of the foot is generated in advance by inputting the feature amount extracted from the time-series data of the pitch angle at the terminal stance period and the CPEI. For example, according to the present example embodiment, an average value, an integral value, or the like of an arithmetic average, a weighted average, or the like of the pitch angle in the period of the terminal stance period extracted from the time-series data of the pitch angle in the terminal stance period is used as the feature amount. For example, according to the present example embodiment, for a plurality of subjects, a large amount of data having a pitch angle as an explanatory variable and CPEI as an objective variable is measured, and the presumption model is generated by learning the data as teacher data. For example, according to the present example embodiment, the presumption model is generated in which the state of the foot is classified into one of pronation, supination, and normal according to the value of CPEI, and output as the degree of pronation/supination of the foot.

Figure 10:
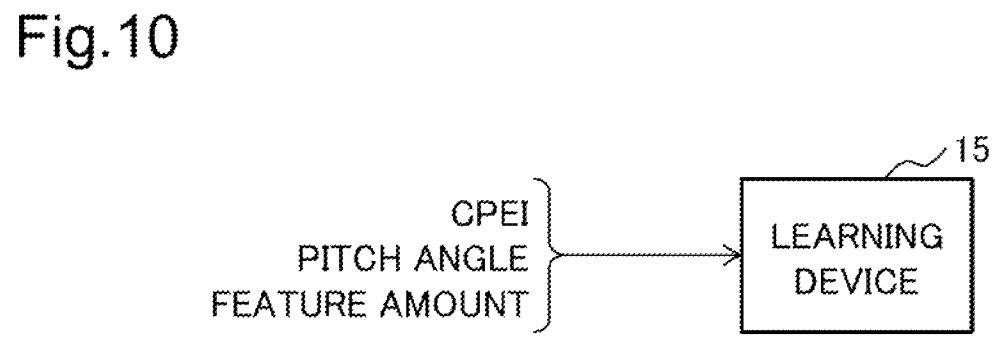

FIG. 10 is a conceptual diagram illustrating an example of causing a learning device 15 to learn the feature amount of the pitch angle at the terminal stance period as the explanatory variable and the data set of the CPEI as the objective variable as the teacher data. According to the present example embodiment, the learning device 15 is caused to learn teacher data regarding a plurality of subjects, and the presumption model that outputs an estimation result regarding the degree of pronation/supination of the foot according to the input of the feature amount of the pitch angle at the terminal stance period is generated in advance. The estimation result output by the presumption model will be described later.

The presumption model generated in advance is stored in the estimation device 12. For example, the presumption model may be stored in the estimation device 12 at the time of factory shipment of a product, calibration before the user uses the estimation device 12, or the like. The estimation device 12 estimates the degree of pronation/supination of the foot by inputting, to the presumption model, the feature amount extracted from the time-series data of the pitch angle in the terminal stance period measured by the data acquisition device 11. For example, the estimation device 12 outputs an estimation result classified into any of three classifications of supination, normal, and pronation as the degree of pronation/supination of the foot. For example, the estimation device 12 may output an estimation value of CPEI or a feature amount of the pitch angle in the terminal stance period as the degree of pronation/supination of the foot.

Figure 11:
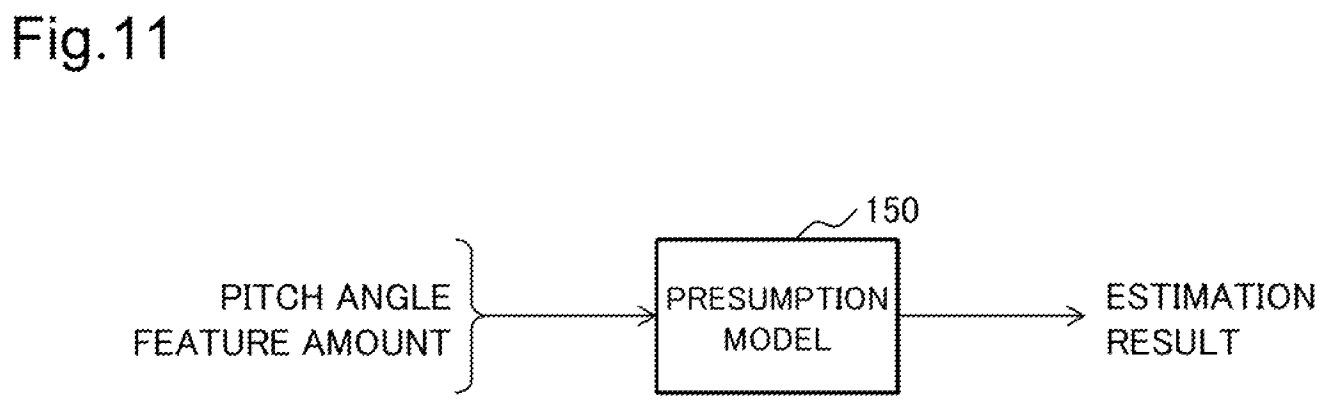

FIG. 11 is a conceptual diagram illustrating an example in which the estimation result regarding the degree of pronation/supination of the foot is output by inputting the feature amount of the pitch angle in the terminal stance period to the presumption model 150 generated in advance. For example, the estimation result regarding the degree of pronation/supination of the foot includes a determination result of the pronation/supination/normal of the foot. For example, the estimation result regarding the degree of pronation/supination of the foot includes recommendation information for advancing a hospital suitable for examination according to the determination result of the pronation/supination/normal of the foot. For example, the estimation result regarding the degree of pronation/supination of the foot may be a value of the pitch angle or CPEI. Note that the above estimation result is an example, and does not limit the estimation result output from the presumption model 150 by inputting the feature amount of the pitch angle at the terminal stance period.

[Data Acquisition Device]

Figure 12:
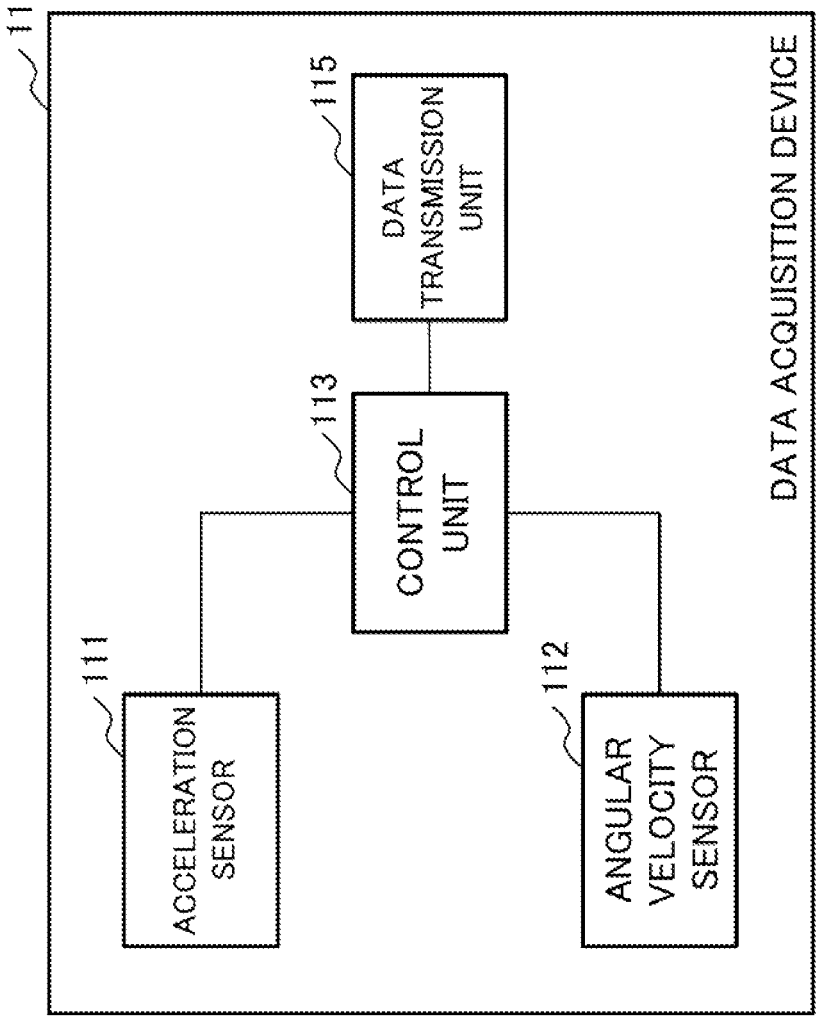
FIG. 12 is a block diagram illustrating an example of a configuration of a data acquisition device of the estimation system according to the first example embodiment.

Next, a detailed configuration of the data acquisition device 11 will be described with reference to the drawings. FIG. 12 is a block diagram illustrating an example of a detailed configuration of the data acquisition device 11. The data acquisition device 11 includes an acceleration sensor 111, an angular velocity sensor 112, a control unit 113, and a data transmission unit 115. In addition, the data acquisition device 11 includes a power supply (not illustrated).

The acceleration sensor 111 is a sensor that measures acceleration (also referred to as spatial acceleration) in three axial directions. The acceleration sensor 111 outputs the measured acceleration to the control unit 113. For example, a sensor of a piezoelectric type, a piezoresistive type, a capacitance type, or the like can be used as the acceleration sensor 111. Note that the sensor used for the acceleration sensor 111 is not limited to the measurement method as long as the sensor can measure acceleration.

The angular velocity sensor 112 is a sensor that measures angular velocity (also referred to as spatial angular velocity) in three axial directions. The angular velocity sensor 112 outputs the measured angular velocity to the control unit 113. For example, a sensor of a vibration type, a capacitance type, or the like can be used as the angular velocity sensor 112. Note that the sensor used for the angular velocity sensor 112 is not limited to the measurement method as long as the sensor can measure the angular velocity.

The control unit 113 acquires each of acceleration and angular velocity in three axial directions from each of the acceleration sensor 111 and the angular velocity sensor 112. The control unit 113 converts the acquired acceleration and angular velocity into digital data, and outputs the converted digital data (also referred to as sensor data) to the data transmission unit 115. The sensor data includes at least the acceleration data (including acceleration vectors in three axial directions) obtained by converting acceleration of analog data into digital data and the angular velocity data (including angular velocity vectors in three axial directions) obtained by converting angular velocity of analog data into digital data. Note that the acceleration data and the angular velocity data are associated with the times of acquiring those pieces of data.

Furthermore, the control unit 113 may be configured to output sensor data obtained by adding correction such as a mounting error, temperature correction, and linearity correction to the acquired acceleration data and angular velocity data. Furthermore, the control unit 113 may generate angle data in three axial directions using the acquired acceleration data and angular velocity data.

For example, the control unit 113 is a microcomputer or a microcontroller that performs overall control and data processing of the data acquisition device 11. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on physical quantities (analog data) such as the measured angular velocity and acceleration, and stores the converted digital data in the flash memory. Note that the physical quantity (analog data) measured by the acceleration sensor 111 and the angular velocity sensor 112 may be converted into digital data in each of the acceleration sensor 111 and the angular velocity sensor 112. The digital data stored in the flash memory is output to the data transmission unit 115 at a predetermined timing.

The data transmission unit 115 acquires the sensor data from the control unit 113. The data transmission unit 115 transmits the acquired sensor data to the estimation device 12. The data transmission unit 115 may transmit the sensor data to the estimation device 12 via a wire such as a cable, or may transmit the sensor data to the estimation device 12 via wireless communication. For example, the data transmission unit 115 is configured to transmit the sensor data to the estimation device 12 via a wireless communication function (not illustrated) conforming to a standard such as Bluetooth (registered trademark) or WiFi (registered trademark). Note that the communication function of the data transmission unit 115 may conform to a standard other than Bluetooth (registered trademark) or WiFi (registered trademark).

[Estimation Device]

Figure 13:
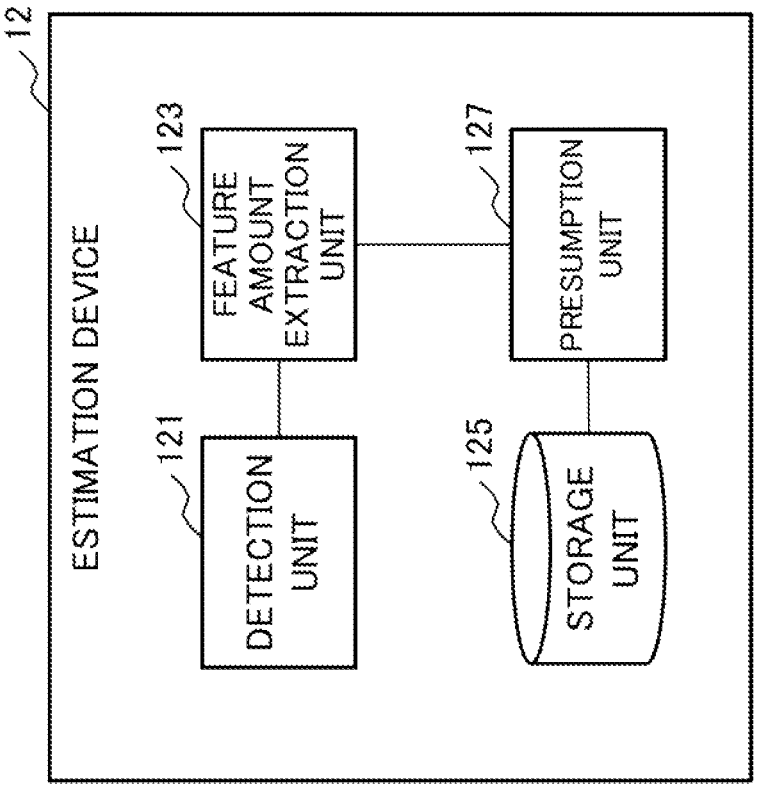
FIG. 13 is a block diagram illustrating an example of a configuration of the estimation device of the estimation system according to the first example embodiment.

Next, a detailed configuration of the estimation device 12 included in the estimation system 1 will be described with reference to the drawings. FIG. 13 is a block diagram illustrating an example of a configuration of the estimation device 12. The estimation device 12 includes a detection unit 121, a feature amount extraction unit 123, a storage unit 125, and a presumption unit 127.

The detection unit 121 acquires sensor data from the data acquisition device 11 installed on the footwear. The detection unit 121 uses the sensor data to generate time-series data associated with a gait of the walker wearing the footwear on which the data acquisition device 11 is installed. The detection unit 121 extracts gait waveform data for one gait cycle from the generated time-series data. For example, the detection unit 121 detects a period of 30 to 50% as the terminal stance period in the gait waveform having the pitch angle for one gait cycle starting from the heel strike. For example, the detection unit 121 detects timing (start point) of heel lift and timing (end point) of opposite heel strike from the extracted gait waveform data, and detects a period between the two as a terminal stance period. For example, the detection unit 121 detects the timing of the heel lift or the opposite foot heel strike based on the acceleration inflection point included in the gait waveform of the roll angular acceleration.

For example, the detection unit 121 acquires sensor data from the data acquisition device 11. The detection unit 121 converts the coordinate system of the acquired sensor data from the local coordinate system to the world coordinate system. When the user is standing upright, the local coordinate system (x-axis, y-axis, z-axis) and the world coordinate system (X axis, Y axis, Z axis) coincide. While the user is walking, since the spatial orientation of the data acquisition device 11 changes, the local coordinate system (x-axis, y-axis, z-axis) and the world coordinate system (X axis, Y axis, Z axis) do not match. Therefore, the detection unit 121 converts the sensor data acquired by the data acquisition device 11 from the local coordinate system (x-axis, y-axis, z-axis) of the data acquisition device 11 into the world coordinate system (X axis, Y axis, Z axis).

For example, the detection unit 121 generates time-series data such as spatial acceleration and spatial angular velocity. Furthermore, the detection unit 121 integrates the spatial acceleration and the spatial angular velocity, and generates time-series data such as the spatial velocity, the spatial angle (foot sole angle), and the spatial trajectory. These pieces of time-series data are relevant to the gait waveforms. The detection unit 121 generates time-series data at a predetermined timing or time interval set in accordance with a general gait cycle or a gait cycle unique to the user. Any timing can be set as the timing at which the detection unit 121 generates the time-series data. For example, the detection unit 121 is configured to continue to generate time-series data during a period in which gait of the user is continued. Furthermore, the detection unit 121 may be configured to generate time-series data at a specific timing.

The feature amount extraction unit 123 extracts a feature amount from a gait waveform (also referred to as an angular waveform in the coronal plane) of the pitch angle in a period (terminal stance period) in which the timing of the heel lift detected by the detection unit 121 is a start point and the timing of the opposite foot heel strike is an end point. For example, the feature amount extraction unit 123 extracts, as a feature amount, an integral value, an average value, or the like of the pitch angle in the terminal stance period from the gait waveform of the pitch angle (angular waveform in the coronal plane).

The storage unit 125 stores the presumption model 150 generated in advance. The presumption model 150 outputs an estimation result regarding the degree of pronation/supination of the foot according to the input of the feature amount of the pitch angle in the terminal stance period. For example, the presumption model 150 outputs the determination result of the pronation/supination/normal of the foot as the estimation result regarding the degree of pronation/supination of the foot in response to the input of the feature amount of the pitch angle at the terminal stance period.

For example, in response to the input of the feature amount of the pitch angle at the terminal stance period, the presumption model 150 outputs, as the estimation result regarding the degree of pronation/supination of the foot, recommendation information for advancing a hospital suitable for medical examination according to the determination result of the pronation/supination/normal of the foot. For example, the presumption model 150 outputs the value of the pitch angle and CPEI as the estimation result regarding the degree of pronation/supination of the foot in response to the input of the feature amount of the pitch angle at the terminal stance period. Note that the estimation result of the presumption model 150 described above is an example, and does not limit the estimation result output from the presumption model 150 by inputting the feature amount of the pitch angle at the terminal stance period.

The presumption unit 127 inputs the feature amount of the gait waveform (angular waveform in the coronal plane) of the pitch angle in the terminal stance period extracted by the feature amount extraction unit 123 to the presumption model 150, and estimates the estimation result regarding the degree of pronation/supination of the foot. The presumption unit 127 outputs the estimation result. The estimation result by the presumption unit 127 is output to a host system, a server in which a database is constructed, a mobile terminal of a user who is an acquisition source of the gait waveform, or the like. The output destination of the estimation result by the presumption unit 127 is not particularly limited.

(Operation)

Figure 14:
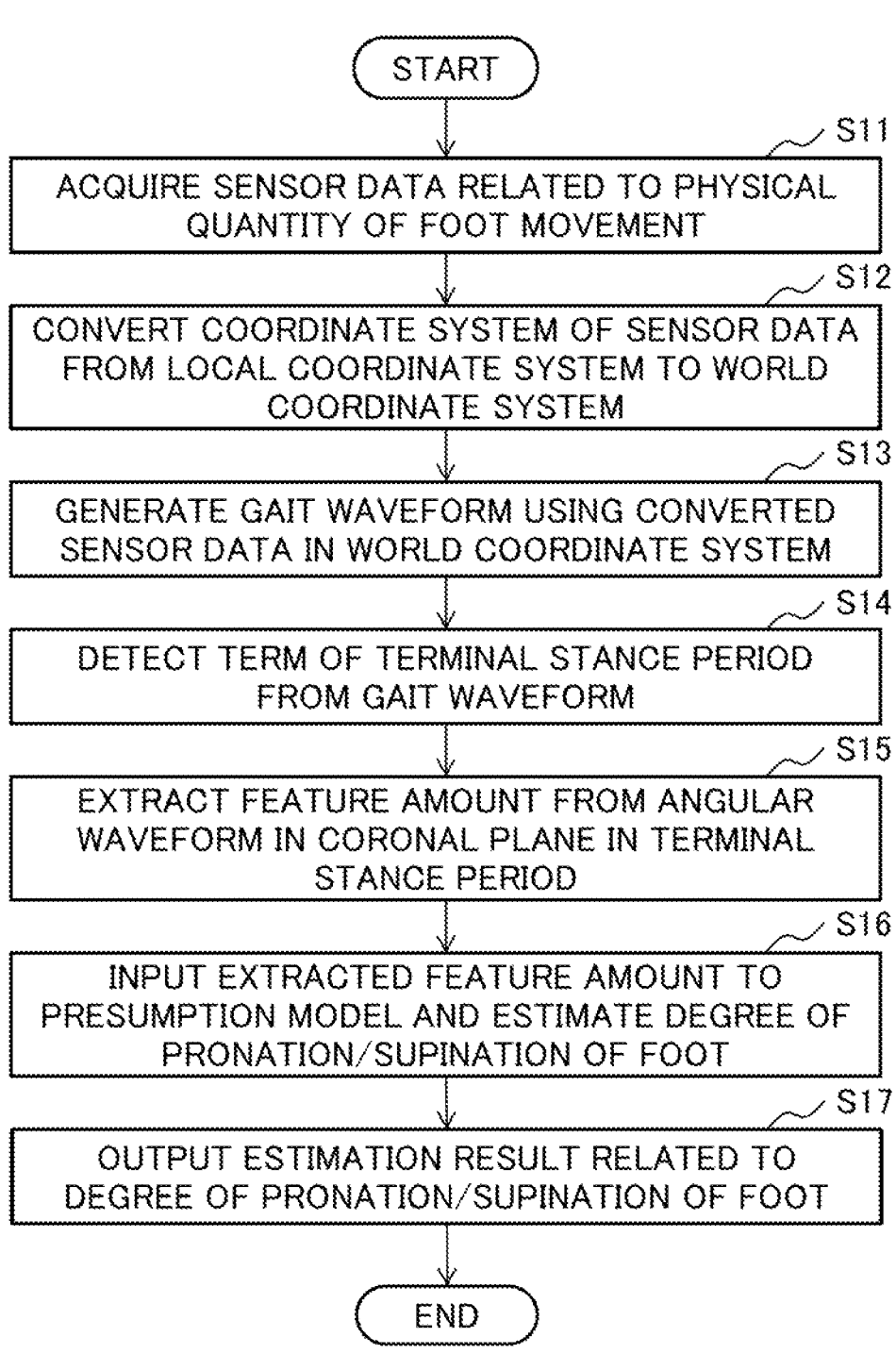
FIG. 14 is a flowchart for explaining an example of the operation of the estimation device of the estimation system according to the first example embodiment.

Next, an operation of the estimation device 12 of the estimation system 1 according to the present example embodiment will be described with reference to the drawings. FIG. 14 is a flowchart for explaining an outline of the operation of the estimation device 12. The detailed operation of the estimation device 12 is as described regarding the above-described configuration.

In FIG. 14, first, the estimation device 12 acquires sensor data regarding a physical quantity related to the motion of the foot from the data acquisition device 11 (step S11).

Next, the estimation device 12 converts the coordinate system of the acquired sensor data from the local coordinate system set in the data acquisition device 11 to the world coordinate system (step S12).

Next, the estimation device 12 generates a gait waveform using the time-series data of the sensor data after conversion into the world coordinate system (step S13).

Next, the estimation device 12 detects the term of the terminal stance period from the gait waveform (step S14).

Next, the estimation device 12 extracts the feature amount from the angular waveform of the coronal plane (gait waveform of the pitch angle) at the terminal stance period with the timing of the heel lift as the start point and the timing of the opposite toe release as the end point (step S15).

Next, the estimation device 12 inputs the extracted feature amount to the presumption model, and estimates the degree of pronation/supination of the foot (step S16).

Next, the estimation device 12 outputs an estimation result regarding the degree of pronation/supination of the foot (step S17).

Verification Example

Figure 15:
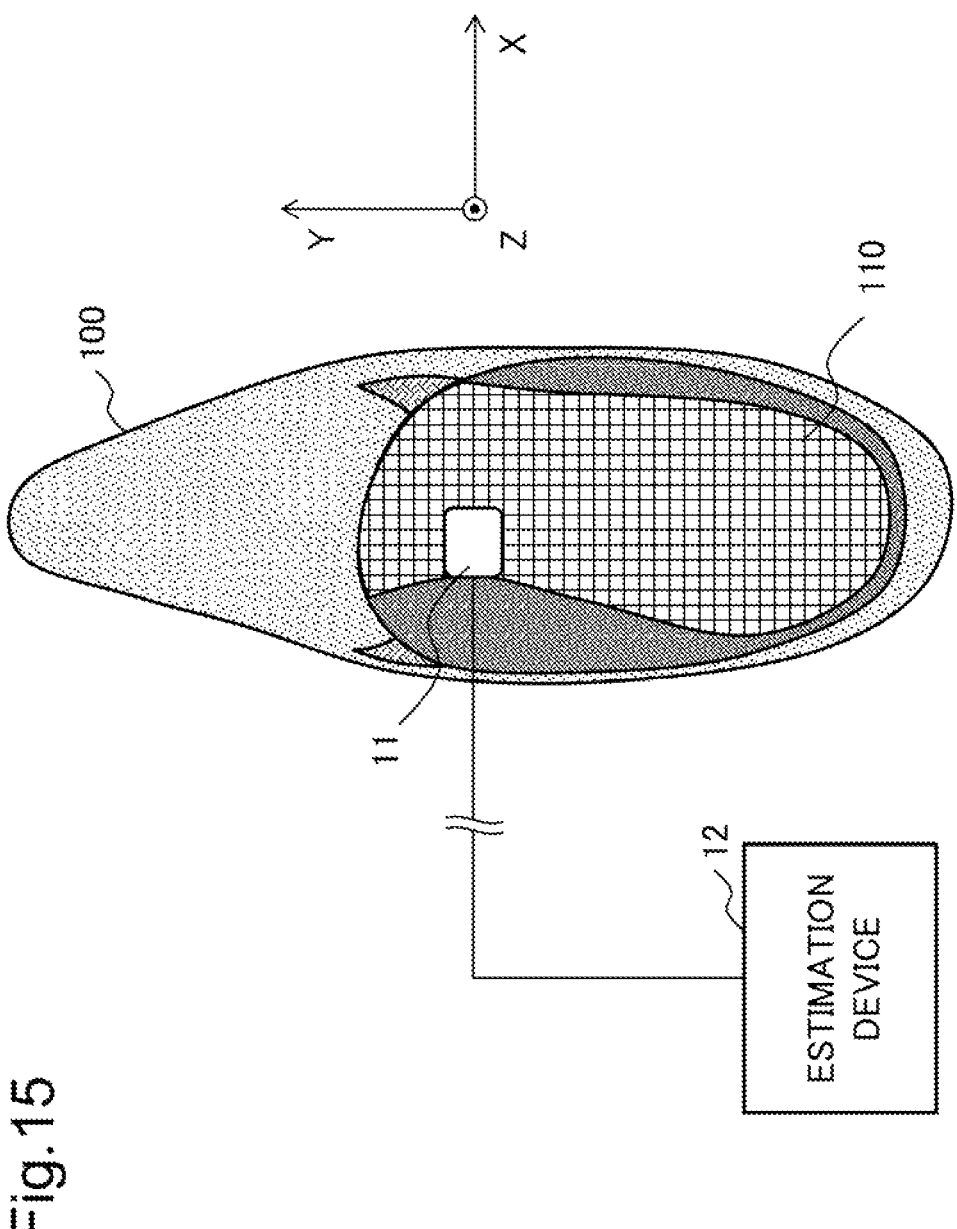
FIG. 15 is a conceptual diagram illustrating an example in which the data acquisition device and a pressure-sensitive sheet of the estimation system according to the first example embodiment are disposed in the footwear.

Next, a verification example of verifying the relationship between the feature amount extracted from the gait waveform of the pitch angle based on the sensor data measured by the data acquisition device 11 and the measured value of the CPEI will be described. FIG. 15 is a conceptual diagram illustrating an arrangement example of a pressure-sensitive sensor 110 and the data acquisition device 11 used in this verification example. According to the present verification example, the pressure-sensitive sensor 110 capable of measuring the foot pressure distribution was inserted as an insole of the shoe 100, and the data acquisition device 11 was mounted at a position on the back side of the arch. In this verification example, data for a total of 14 feet was collected for seven subjects. For the collected data, a moving average value of data for ten steps was used for verification. In this verification example, the relationship between the feature amount extracted from the time-series data of the pitch angle and the measured value (true value) of the CPEI was verified.

Figure 16:
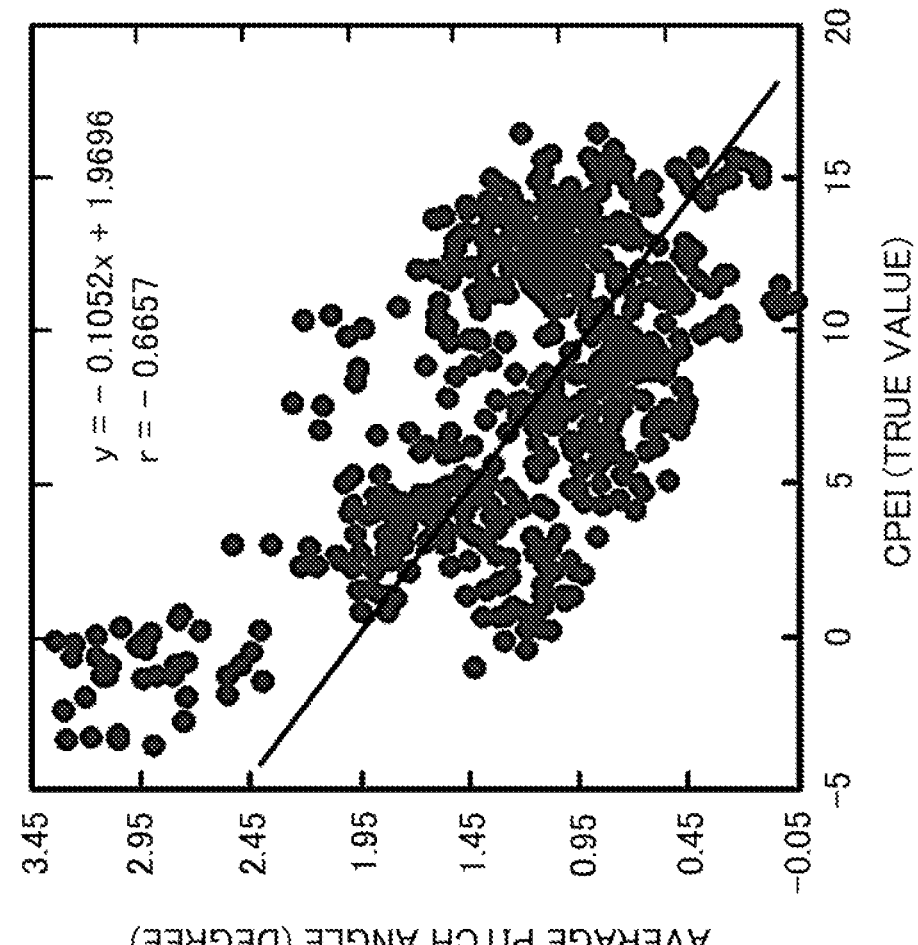
FIG. 16 is a graph in which a feature amount extracted from a gait waveform of a pitch angle based on sensor data measured by the data acquisition device of the estimation system according to the first example embodiment is associated with CPEI (true value) calculated based on a pressure distribution measured by a pressure-sensitive sensor.

FIG. 16 is a graph in which CPEI (true value) calculated based on the pressure distribution measured by the pressure-sensitive sensor 110 is associated with the feature amount extracted from the gait waveform of the pitch angle based on the sensor data measured by the data acquisition device 11. In FIG. 16, the average value of the pitch angle in the terminal stance period is associated with CPEI (true value) as a feature amount. The regression line obtained by associating the CPEI (true value) with the average value of the pitch angle at the terminal stance period had a slope of −0.1052, an intercept of 1.9696, and a correlation coefficient r of −0.6657. In addition, root mean square error (RMSE) was calculated for the relationship between the average value of the pitch angle and CPEI (true value) at the terminal stance period using leave one subject out cross validation. As a result, the RMSE of the average value of the pitch angle and the CPEI (true value) at the terminal stance period was 3.542.

Figure 17:
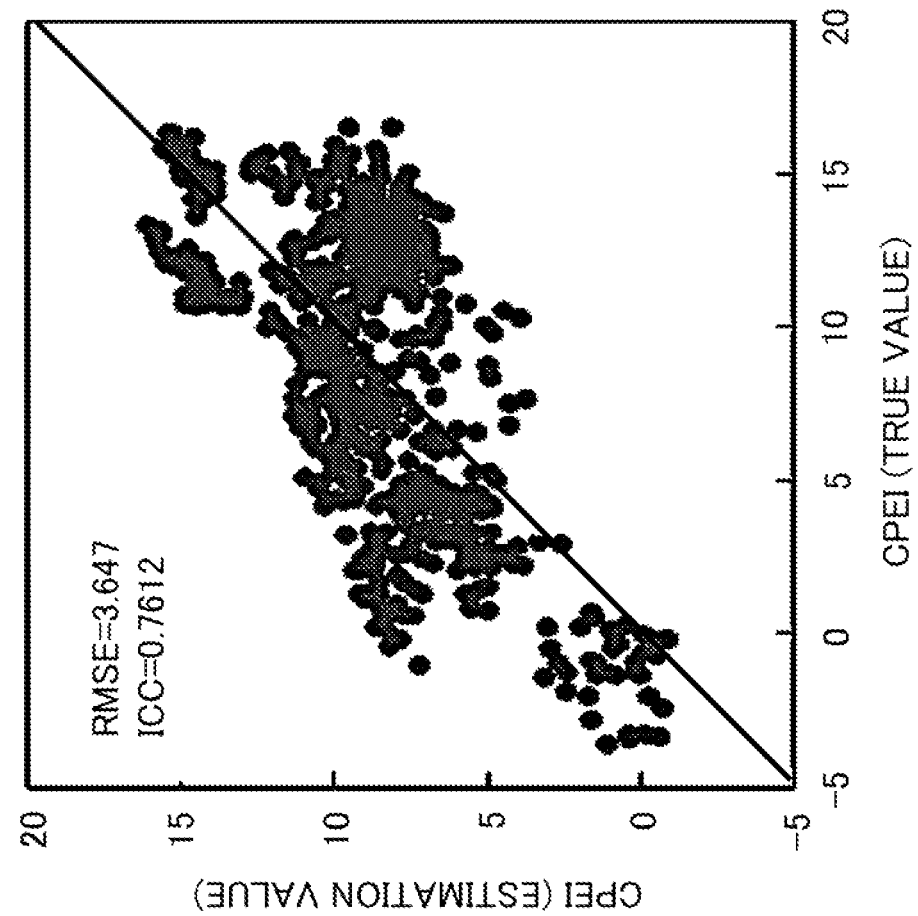
FIG. 17 is a graph in which CPEI (estimation value) estimated by the estimation device of the estimation system of the first example embodiment is associated with CPEI (true value) calculated based on the pressure distribution measured by the pressure-sensitive sensor.

FIG. 17 is a graph in which a regression line derived from the graph of FIG. 16 is used as a presumption model, and CPEI (estimation value), which is an output when the average value of the pitch angle in the terminal stance period is input to the presumption model, is associated with CPEI (true value). RMSE was calculated for the relationship between CPEI (estimation value) and CPEI (true value) using leave one subject out cross-validation. As a result, the RMSE was 3.647 for CPEI (estimation value) and CPEI (true value). In addition, the intraclass correlation coefficient (ICC) relating to the verification of FIG. 17 was 0.7612, and high reliability was obtained.

As described above, in the present verification example, a reliable correlation was obtained between the CPEI (estimation value) estimated using the feature amount extracted from the gait waveform of the pitch angle based on the measurement result of the data acquisition device 11 and the CPEI (true value) based on the measurement result of the pressure-sensitive sensor 110.

Application Example

Next, an application example of the estimation system 1 according to the present example embodiment will be described with reference to the drawings. In the present application example, an estimation result regarding the degree of pronation/supination of the foot output by the estimation device 12 is displayed on a display device or utilized as big data. In the following example, it is assumed that the data acquisition device 11 is installed in a shoe of a walker, and sensor data based on a physical quantity related to movement of a foot measured by the data acquisition device 11 is transmitted to a mobile terminal possessed by the walker. The sensor data transmitted to the mobile terminal is subjected to data processing by application software or the like installed in the mobile terminal.

Figure 18:
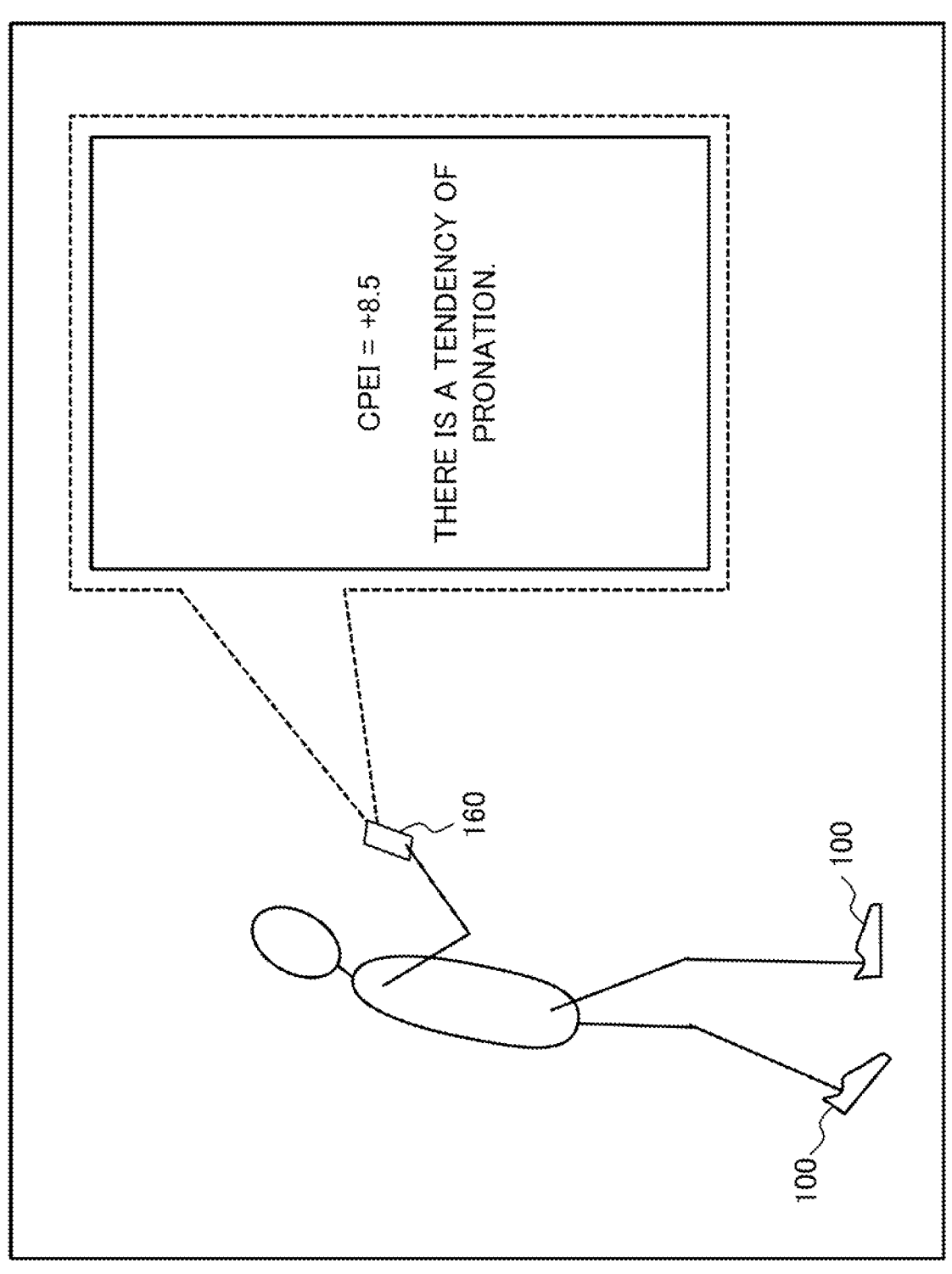
FIG. 18 is a conceptual diagram illustrating an example in which information based on the estimation result regarding the degree of pronation/supination of the foot estimated by the estimation device of the estimation system according to the first example embodiment is displayed on a display unit of a mobile terminal.

FIG. 18 illustrates an example in which the estimation result regarding the degree of pronation/supination of the foot of the walker is displayed on the screen of a mobile terminal 160 of the walker wearing the shoe 100 in which the data acquisition device (not illustrated) is installed. In the example of FIG. 18, a numerical value of "CPEI=+8.5" and a notification of "There is a tendency of pronation" are displayed on the screen of the mobile terminal 160 as the estimation result regarding the degree of pronation/supination of the foot. The walker who has seen the estimation result regarding the degree of pronation/supination of the foot displayed on the screen of the mobile terminal 160 can take an action according to the estimation result. For example, the walker who has seen the estimation result regarding the degree of pronation/supination of the foot displayed on the screen of the mobile terminal 160 can contact a medical institution or the like regarding his/her situation according to the estimation result. For example, the walker who has seen the estimation result regarding the degree of pronation/supination of the foot displayed on the screen of the mobile terminal 160 can exercise or walk in a manner suitable for the walker according to the estimation result.

Figure 19:
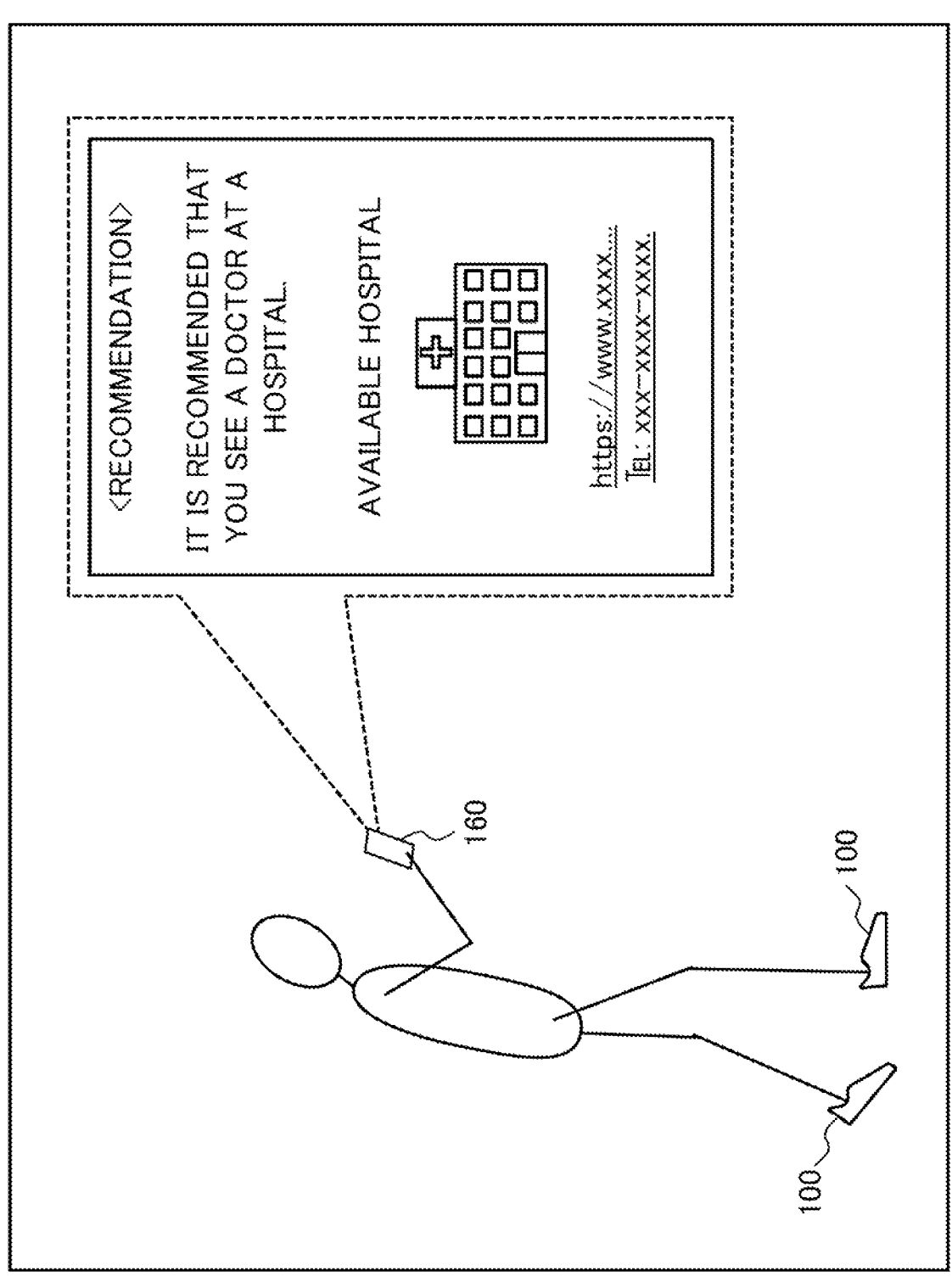
FIG. 19 is a conceptual diagram illustrating another example of displaying information based on the estimation result regarding the degree of pronation/supination of the foot estimated by the estimation device of the estimation system according to the first example embodiment on the display unit of the mobile terminal.

FIG. 19 illustrates an example in which information according to the estimation result regarding the degree of pronation/supination of the foot of the walker is displayed on the screen of the mobile terminal 160 of the walker wearing the shoe 100 on which the data acquisition device (not illustrated) is installed. For example, information recommending that the walker see a doctor at a hospital is displayed on the screen of the mobile terminal 160 according to the progress status of the pronation/supination of the foot. For example, depending on the progress status of the pronation/supination of the foot, a link to a site or a telephone number of a hospital where a medical examination is available may be displayed on the screen of the mobile terminal 160. For example, the walker who has seen the information related to the estimation result regarding the degree of pronation/supination of the foot displayed on the screen of the mobile terminal 160 can act according to the information.

Figure 20:
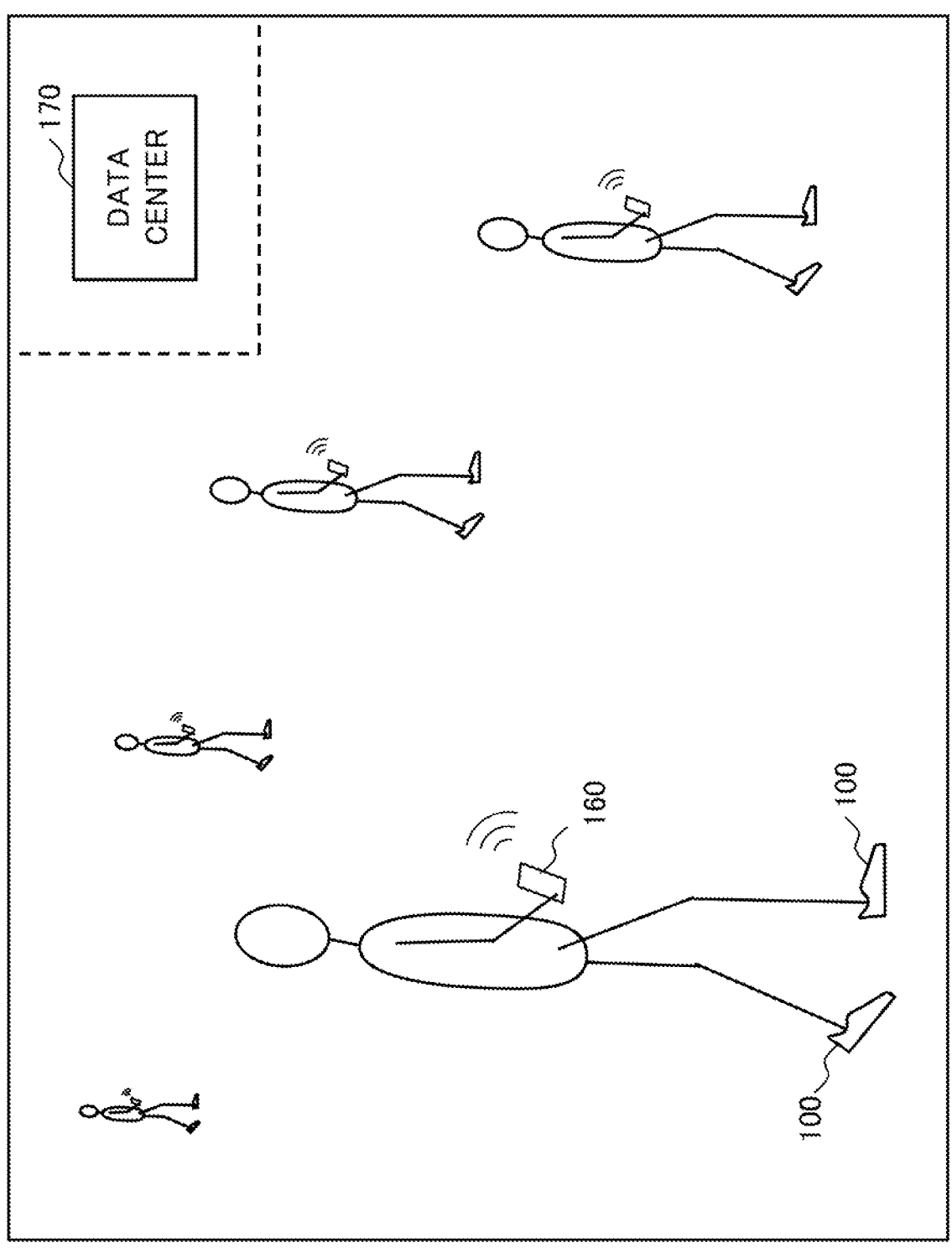
FIG. 20 is a conceptual diagram illustrating an example in which data based on the estimation result regarding the degree of pronation/supination of the foot estimated by the estimation device of the estimation system according to the first example embodiment is transmitted to a data center.
Figure 22:
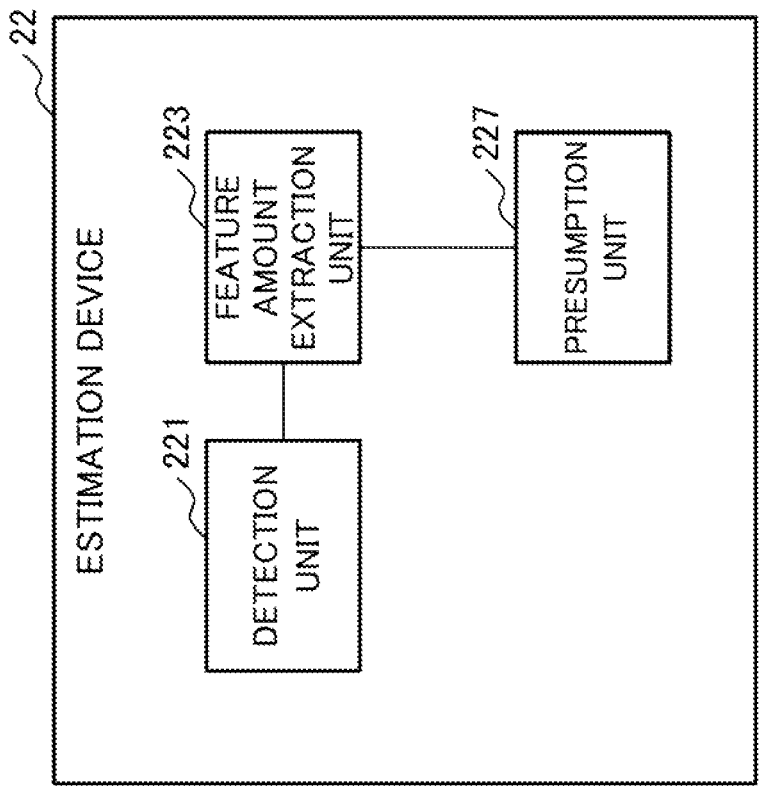
FIG. 22 is a block diagram illustrating an example of a configuration of an estimation device according to a second example embodiment.

FIG. 20 illustrates an example in which information based on sensor data measured by a data acquisition device (not illustrated) is transmitted from mobile terminals 160 of a plurality of walkers wearing shoes 100 in which the data acquisition device is installed to a data center 170. For example, the mobile terminal 160 transmits sensor data measured by the data acquisition device, an estimation value of CPEI, and an estimation result regarding the degree of pronation/supination of the foot of the walker to the data center 170. For example, data transmitted to the data center 170 is accumulated in a database.

FIG. 21 illustrates an example (a table 171) of the information transmitted to the data center 170 and accumulated in the database. For example, in the table 171, an estimation value of CPEI estimated for each user is stored in association with information such as a maker of the shoe 100, a type of the shoe 100, and date and time of measurement. The data stored in the table 171 can be utilized as big data. For example, the data stored in the table 171 is used as statistical data for each type of footwear. For example, the data accumulated in the database is used for designing shoes. For example, if the estimation value of CPEI for each shoe is accumulated and the temporal change of the estimation value of CPEI for each shoe is verified, there is a possibility that the temporal change of the shoe can be monitored. For example, with respect to the data of the user A, it is assumed that when the footwear X1 of X Company is continuously worn for about one year, the estimation value of CPEI increases from +8.2 to +9.5. In a case where a similar tendency is observed with respect to other users, in the X Company, it is only required to design the shoe such that the temporal change of the estimation value of CPEI shifts to the negative side. Similarly, regarding shoes of other companies, by accumulating and verifying estimation values of CPEI of a plurality of users, it is possible to monitor a tendency of a temporal change unique to the shoes. Furthermore, the data stored in the table 171 may be used to monitor the progress status of the pronation/supination of the foot for each user. For example, for a user whose CPEI estimation value changes over time deviates from the average trend, there is a possibility that the pronation/supination of the foot has progressed. In such a case, a notification to recommend the user to visit a hospital may be transmitted according to the tendency of the temporal change of the estimation value of CPEI. The data stored in the table 171 and how to use the data are not limited to the above examples.

As described above, the estimation system according to the present example embodiment includes the data acquisition device and the estimation device. The data acquisition device measures the spatial acceleration and the spatial angular velocity, generates sensor data based on the measured spatial acceleration and spatial angular velocity, and transmits the generated sensor data to the estimation device. The estimation device includes a detection unit, a feature amount extraction unit, and a presumption unit. The detection unit detects the period of the terminal stance period from the time-series data of the sensor data based on the physical quantity related to the movement of the foot measured by the data acquisition device installed in the foot portion. The feature amount extraction unit extracts a feature amount from the angular waveform in the coronal plane in the term of the terminal stance period. The presumption unit estimates the degree of pronation/supination of the foot using the feature amount extracted from the angular waveform in the coronal plane.

The estimation system according to the present example embodiment can estimate the degree of pronation/supination of the foot based on the physical quantity related to the movement of the foot measured by the data acquisition device installed in the foot portion. That is, according to the estimation system of the present example embodiment, the degree of pronation/supination of the foot can be estimated with a simple configuration.

In one aspect of the present example embodiment, the presumption unit inputs the feature amount extracted from the angular waveform in the coronal plane to the presumption model, and outputs an estimation result regarding the degree of pronation/supination of the foot. The presumption model outputs an estimation result regarding the degree of pronation/supination of the foot when the feature amount extracted from the angular waveform in the coronal plane is input. For example, the presumption unit uses the presumption model which has learned a data set in which the feature amount extracted from the angular waveform in the coronal plane is used as an explanatory variable and the center of pressure excursion index obtained from the foot pressure distribution measured by the pressure sensor is used as an objective variable.

According to an aspect of the present example embodiment, the presumption unit outputs the estimation result indicating one of pronation/supination of the foot and normal foot according to a value of the center of pressure excursion index. For example, the presumption unit outputs the estimation result indicating supination when the center of pressure excursion index value is equal to or more than 20, outputs the estimation result indicating normality when the center of pressure excursion index value is equal to or more than 9 and less than 20, and outputs the estimation result indicating pronation when the center of pressure excursion index value is less than 9.

For example, the detection unit extracts a gait waveform for one gait cycle stating from heel strike, from the time-series data of the sensor data, and detects a period of 30 to 50% of the extracted gait waveform as the terminal stance period. For example, the detection unit detects timing of heel lift and timing of an opposite heel strike from the time-series data of the sensor data, and detects a period from the timing of heel lift to the timing of the opposite heel strike is detected as a period of the terminal stance period.

For example, the detection system according to the present example embodiment can be applied to an order-made shoe. For example, the detection system according to the present example embodiment can be applied to the use of causing the user to walk while wearing the guest shoes in which the data acquisition device is installed, and verifying the degree of pronation/supination of the foot of the user. If the data related to the verification result of the degree of pronation/supination of the foot of the user is provided to the maker who designs the shoe, the shoe can be designed according to the degree of pronation/supination of the foot of the user.

For example, the detection system according to the present example embodiment can also be applied to an application of monitoring daily life of a user. For example, if a gait habit can be extracted or a change in shoes can be recommended according to the progress status of the pronation/supination of the foot in a gait of the user, there is a possibility that the progress of the pronation/supination of the foot of the user can be suppressed. For example, if the user is using a foot pronation/supination orthodontic appliance, providing the user with information according to the degree of pronation/supination of the foot may reduce the progression of symptoms or prevent injury.

For example, according to the detection system of the present example embodiment, by collecting estimation results of a large number of users and constructing a database of estimation results regarding the degree of pronation/supination of the foot, there is a possibility that information regarding the degree of pronation/supination of the foot can be utilized as big data. For example, if the degrees of pronation/supination and CPEI of the feet of a large number of users are stored in a database in association with shoes, data that can be utilized for shoe design, maintenance, and the like can be accumulated.

Second Example Embodiment

Figure 23:
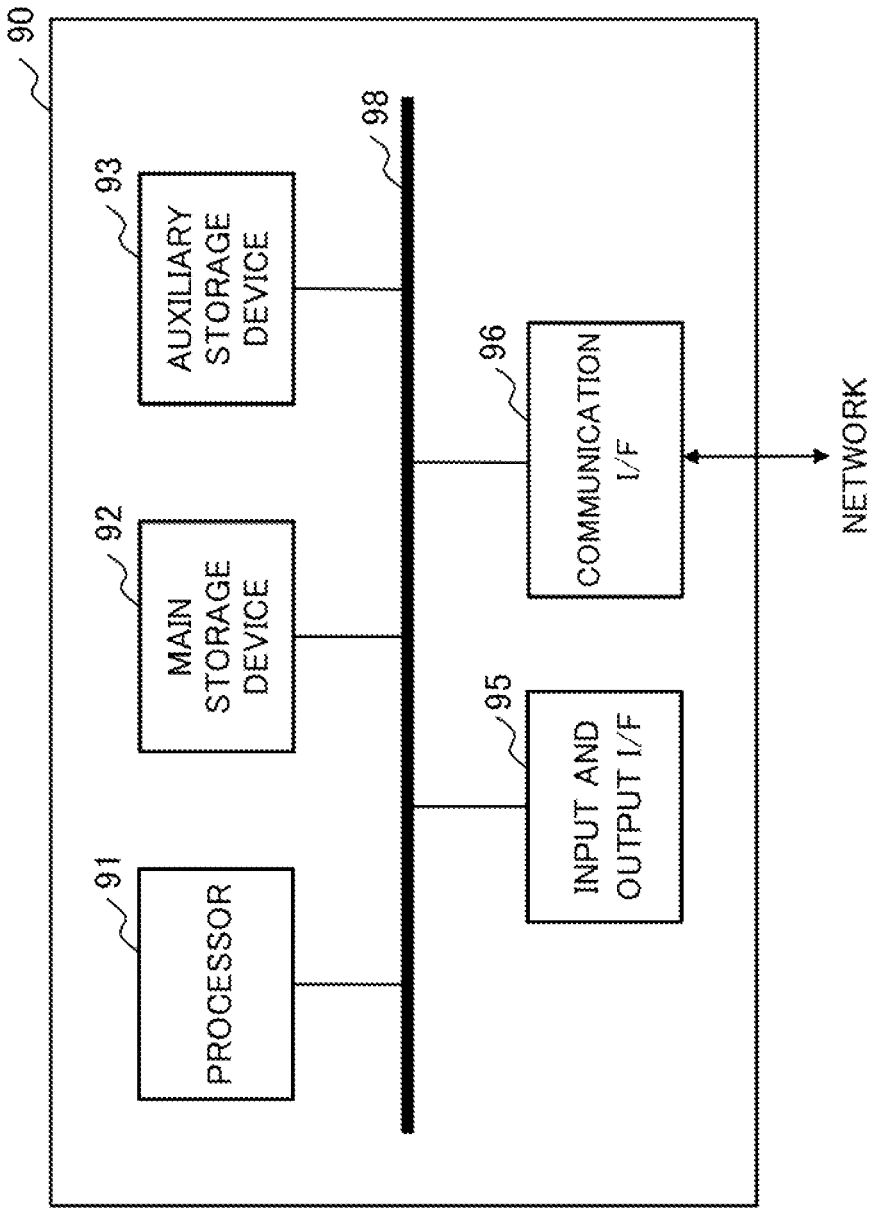
FIG. 23 is a block diagram illustrating an example of a hardware configuration for implementing the estimation device according to each example embodiment.

Next, an estimation device according to a second example embodiment will be described with reference to the drawings. The estimation device according to the present example embodiment has a configuration which is simplified from the estimation device of the first example embodiment. FIG. 23 is a block diagram illustrating an example of a configuration of the estimation device 22 according to the present example embodiment. The estimation device 22 includes a detection unit 221, a feature amount extraction unit 223, and a presumption unit 227.

The detection unit 221 detects the term of the terminal stance period from the time-series data of the sensor data based on the physical quantity related to the movement of the foot measured by the sensor installed in the foot portion. The feature amount extraction unit 223 extracts a feature amount from the angular waveform in the coronal plane in the term of the terminal stance period. The presumption unit 227 estimates the degree of pronation/supination of the foot using the feature amount extracted from the angular waveform in the coronal plane.

The estimation device according to the present example embodiment can estimate the degree of pronation/supination of the foot based on the physical quantity related to the movement of the foot measured by the sensor installed in the foot portion. In other words, according to the estimation device of the present example embodiment, the degree of pronation/supination of the foot can be estimated with a simple configuration.

(Hardware)

Here, a hardware configuration for executing the processing of the estimation device according to each example embodiment of the present invention will be described using an information processing device 90 of FIG. 23 as an example. Note that the information processing device 90 in FIG. 23 is a configuration example for executing processing of the estimation device of each example embodiment, and does not limit the scope of the present invention.

As illustrated in FIG. 23, the information processing device 90 includes a processor 91, a main storage device 92, an auxiliary storage device 93, an input/output interface 95, and a communication interface 96. In FIG. 23, the interface is abbreviated as I/F. The processor 91, the main storage device 92, the auxiliary storage device 93, the input/output interface 95, and the communication interface 96 are data-communicably connected to each other via a bus 98. In addition, the processor 91, the main storage device 92, the auxiliary storage device 93, and the input/output interface 95 are connected to a network such as the Internet or an intranet via the communication interface 96.

The processor 91 develops, in the main storage device 92, a program stored in the auxiliary storage device 93 or the like and executes the developed program. According to the present example embodiment, a software program installed in the information processing device 90 may be used. The processor 91 executes processing by the estimation device according to the present example embodiment.

The main storage device 92 has an area in which a program is developed. The main storage device 92 may be a volatile memory such as a dynamic random access memory (DRAM). In addition, a nonvolatile memory such as a magnetoresistive random access memory (MRAM) may be configured/added as the main storage device 92.

The auxiliary storage device 93 stores various data. The auxiliary storage device 93 includes a local disk such as a hard disk or a flash memory. Note that various data may be stored in the main storage device 92, and the auxiliary storage device 93 may be omitted.

The input/output interface 95 is an interface for connecting the information processing device 90 and a peripheral device. The communication interface 96 is an interface for connecting to an external system or device through a network such as the Internet or an intranet based on a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input information and settings. When a touch panel is used as the input device, the display screen of the display device may also serve as the interface of the input device. Data communication between the processor 91 and the input device may be mediated by the input/output interface 95.

Furthermore, the information processing device 90 may be provided with a display device for displaying information. In a case where a display device is provided, the information processing device 90 preferably includes a display control device (not illustrated) for controlling display of the display device. The display device may be connected to the information processing device 90 via the input/output interface 95.

The above is an example of a hardware configuration for enabling the estimation device according to each example embodiment of the present invention. Note that the hardware configuration of FIG. 23 is an example of a hardware configuration for executing arithmetic processing of the estimation device according to each example embodiment, and does not limit the scope of the present invention. In addition, a program for causing a computer to execute processing related to the estimation device according to each example embodiment is also included in the scope of the present invention. Further, a recording medium in which the program according to each example embodiment is recorded is also included in the scope of the present invention. The recording medium can be achieved by, for example, an optical recording medium such as a compact disc (CD) or a digital versatile disc (DVD). Furthermore, the recording medium may be achieved by a semiconductor recording medium such as a universal serial bus (USB) memory or a secure digital (SD) card, a magnetic recording medium such as a flexible disk, or another recording medium. In a case where the program executed by the processor is recorded in the recording medium, the recording medium is relevant to a program recording medium.

The components of the estimation device of each example embodiment can be arbitrarily combined. In addition, the components of the estimation device of each example embodiment may be implemented by software or may be implemented by a circuit.

Although the present invention has been described with reference to the example embodiments, the present invention is not limited to the above example embodiments. Various modifications that can be understood by those skilled in the art can be made to the configuration and details of the present invention within the scope of the present invention.

REFERENCE SIGNS LIST

1 Estimation system
11 Data acquisition device
12, 22 Estimation device
111 Acceleration sensor
112 Angular velocity sensor
113 Control unit
115 Data transmission unit
121, 221 Detection unit
123, 223 Feature amount extraction unit
125 Storage unit
127, 227 Presumption unit

What is claimed is:
1. An estimation device comprising:
an inertial measurement sensor installed on a foot portion, the inertial measurement sensor comprising a three-axis accelerometer and a three-axis gyroscope configured to measure spatial acceleration and spatial angular velocity and output time-series data based on the spatial acceleration and the spatial angular velocity;
at least one memory storing instructions; and
at least one processor connected to the at least one memory and configured to execute the instructions to:
detect a terminal stance period from the time-series data based on a physical quantity related to movement of a foot measured by the inertial measurement sensor provided at the foot portion, the detecting the terminal stance period from the time-series data comprising converting the time-series data from a local coordinate system to a world coordinate system and detecting the terminal stance period as a period from heel lift to opposite heel strike based on an inflection point of roll angular acceleration;
extract a feature amount from an angular waveform in a coronal plane during the terminal stance period, the angular waveform being a pitch angle about a Y-axis in the coronal plane (ZX plane), and the feature amount comprising at least one of an average value, a weighted average value, and an integral value within the terminal stance period;
estimate a degree of pronation/supination of the foot by inputting the feature amount extracted from the angular waveform in the coronal plane to a presumption model, the presumption model generated by learning a data set in which the feature amount extracted from the angular waveform in the coronal plane is an explanatory variable and a center of pressure excursion index (CPEI) obtained from a foot pressure distribution measured by a pressure sensor is an objective variable; and
output the estimation result regarding the degree of pronation/supination of the foot.
2. The estimation device according to claim 1, wherein the at least one processor is configured to execute the instructions to
output the estimation result indicating one of pronation/supination of the foot and a normal foot according to a value of the center of pressure excursion index.
3. The estimation device according to claim 2, wherein the at least one processor is configured to execute the instructions to
output the estimation result indicating supination when the center of pressure excursion index value is equal to or more than 20,
output the estimation result indicating normality when the center of pressure excursion index value is equal to or more than 9 and less than 20, and
output the estimation result indicating pronation when the center of pressure excursion index value is less than 9.
4. The estimation device according to claim 1, wherein the at least one processor is configured to execute the instructions to
extract a gait waveform for one gait cycle starting from heel strike, from the time-series data of the sensor data, and
detect a period of 30 to 50% of the extracted gait waveform as the terminal stance period.
5. The estimation device according to claim 1, wherein the at least one processor is configured to execute the instructions to
detect timing of heel lift and timing of an opposite heel strike from the time-series data of the sensor data, and
detect a period from the timing of heel lift to the timing of the opposite heel strike is detected as the terminal stance period.
6. An estimation system comprising:
the estimation device according to claim 1; and
a data acquisition device configured to measure a spatial acceleration and a spatial angular velocity, generate sensor data based on the measured spatial acceleration and spatial angular velocity, and transmit the generated sensor data to the estimation device.
7. The estimation device according to claim 1,
wherein the presumption model is a machine learning model, and
wherein the processor is further configured to:
perform classification of a degree of pronation/supination based on an output of the machine learning model, and
based on the classification indicating supination or pronation, to output recommendation information that supports user decision-making to visit a hospital.

8. An estimation method that causes a computer to execute processes comprising:

measuring, by an inertial measurement sensor including a three-axis accelerometer and a three-axis gyroscope, spatial acceleration and spatial angular velocity and outputting time-series data based on the spatial acceleration and the spatial angular velocity;

detecting a terminal stance period from the time-series data based on a physical quantity related to a movement of a foot measured by the inertial measurement sensor provided at the foot portion, the detecting the terminal stance period from the time-series data comprising converting the sensor data from a local coordinate system to a world coordinate system and detecting the terminal stance period as a period from heel lift to opposite heel strike based on an inflection point of roll angular acceleration;

extracting a feature amount from an angular waveform in a coronal plane during the terminal stance period, the angular waveform being a pitch angle about a Y-axis in the coronal plane (ZX plane), and the feature amount comprising at least one of an average value, a weighted average value, and an integral value within the terminal stance period;

estimating a degree of pronation/supination of the foot by inputting the feature amount extracted from the angular waveform in the coronal plane to a presumption model, the presumption model generated by learning a data set in which the feature amount extracted from the angular waveform in the coronal plane is an explanatory variable and a center of pressure excursion index (CPE) obtained from a foot pressure distribution measured by a pressure sensor is an objective variable; and outputting the estimation result regarding the degree of pronation/supination of the foot.

9. The estimation method according to claim 8, further comprising:

outputting the estimation result indicating one of pronation/supination of the foot and a normal foot according to a value of the center of pressure excursion index.

10. The estimation method according to claim 9, further comprising:

outputting the estimation result indicating supination when the center of pressure excursion index value is equal to or more than 20, outputting the estimation result indicating normality when the center of pressure excursion index value is equal to or more than 9 and less than 20, and outputting the estimation result indicating pronation when the center of pressure excursion index value is less than 9.

11. The estimation method according to claim 8, further comprising:

extracting a gait waveform for one gait cycle starting from heel strike, from the time-series data of the sensor data, and detecting a period of 30 to 50% of the extracted gait waveform as the terminal stance period.

12. The estimation method according to claim 8, wherein the presumption model is a machine learning model, and wherein the estimation method further comprises:

performing classification of a degree of pronation/supination based on an output of the machine learning model, and based on the classification indicating supination or pronation, outputting recommendation information that supports user decision-making to visit a hospital.

13. A non-transitory program recording medium that stores a program configured to cause a computer to execute one or more processes comprising:

measuring, by an inertial measurement sensor including a three-axis accelerometer and a three-axis gyroscope, spatial acceleration and spatial angular velocity and outputting time-series data based on the spatial acceleration and the spatial angular velocity;

detecting a terminal stance period from the time-series data based on a physical quantity related to a movement of a foot measured by the inertial measurement sensor provided at the foot portion, the detecting the terminal stance period from the time-series data comprising converting the sensor data from a local coordinate system to a world coordinate system and detecting the terminal stance period as a period from heel lift to opposite heel strike based on an inflection point of roll angular acceleration;

extracting a feature amount from an angular waveform in a coronal plane during the terminal stance period, the angular waveform being a pitch angle about a Y-axis in the coronal plane (ZX plane), and the feature amount comprising at least one of an average value, a weighted average value, and an integral value within the terminal stance period;

estimating a degree of pronation/supination of the foot by inputting the feature amount extracted from the angular waveform in the coronal plane to a presumption model, the presumption model generated by learning a data set in which the feature amount extracted from the angular waveform in the coronal plane is an explanatory variable and a center of pressure excursion index (CPE) obtained from a foot pressure distribution measured by a pressure sensor is an objective variable; and outputting the estimation result regarding the degree of pronation/supination of the foot.

14. The non-transitory program recording medium according to claim 13, wherein the one or more processes further comprises:

outputting the estimation result indicating one of pronation/supination of the foot and a normal foot according to a value of the center of pressure excursion index.

15. The non-transitory program recording medium according to claim 14, wherein the one or more processes further comprises: outputting the estimation result indicating supination when the center of pressure excursion index value is equal to or more than 20, outputting the estimation result indicating normality when the center of pressure excursion index value is equal to or more than 9 and less than 20, and outputting the estimation result indicating pronation when the center of pressure excursion index value is less than 9.

16. The non-transitory program recording medium according to claim 13, wherein the one or more processes further comprises:

extracting a gait waveform for one gait cycle starting from heel strike, from the time-series data of the sensor data, and detecting a period of 30 to 50% of the extracted gait waveform as the terminal stance period.

17. The non-transitory program recording medium according to claim 8, wherein the presumption model is a machine learning model, and

wherein the one or more processes further comprises:

performing classification of a degree of pronation/supination based on an output of the machine learning model, and based on the classification indicating supination or pronation, outputting recommendation information that supports user decision-making to visit a hospital.

* * * * *